(12) United States Patent
Willey et al.

(10) Patent No.: US 8,372,258 B2
(45) Date of Patent: Feb. 12, 2013

(54) MONITORING OF ELECTROPLATING ADDITIVES

(75) Inventors: Mark J. Willey, Portland, OR (US); Lian Guo, Baltimore, MD (US); Steven T. Mayer, Lake Oswego, OR (US)

(73) Assignee: Novellus Systems, Inc., Fremont, CA (US)

( * ) Notice: Subject to any disclaimer, the term of this patent is extended or adjusted under 35 U.S.C. 154(b) by 664 days.

(21) Appl. No.: 12/462,354

(22) Filed: Aug. 3, 2009

(65) Prior Publication Data

US 2011/0025338 A1   Feb. 3, 2011

(51) Int. Cl.
*C25D 21/14* (2006.01)
*G01N 27/42* (2006.01)
(52) U.S. Cl. ............ 205/81; 204/434; 205/775
(58) Field of Classification Search ............ 205/81, 205/775
See application file for complete search history.

(56) References Cited

U.S. PATENT DOCUMENTS

| 4,324,621 | A * | 4/1982 | Kerby ............... 205/83 |
| 6,458,262 | B1 | 10/2002 | Reid et al. |
| 7,186,326 | B2 | 3/2007 | Shalyt et al. |
| 7,232,513 | B1 * | 6/2007 | Webb et al. .......... 205/298 |
| 7,270,733 | B2 | 9/2007 | Wikiel et al. |
| 2005/0183958 | A1 | 8/2005 | Wikiel et al. |
| 2008/0264801 | A1 | 10/2008 | West et al. |

FOREIGN PATENT DOCUMENTS

| CA | 988879 | * | 5/1976 |
| JP | 2005-504965 | | 2/2005 |
| KR | 10-2002-0060716 | | 7/2002 |
| WO | WO 2006/110437 | * | 10/2006 |

OTHER PUBLICATIONS

International Search Report and Written Opinion, dated Apr. 22, 2011, issued in International Application No. PCT/US2010/043764.

* cited by examiner

*Primary Examiner* — Patrick Ryan
*Assistant Examiner* — William Leader
(74) *Attorney, Agent, or Firm* — Weaver Austin Villeneuve & Sampson LLP

(57) ABSTRACT

The working electrode in the flow channel of a flow-through electrolytic detection cell is preconditioned by flowing a preconditioning electroplating solution with preconditioner species through the flow channel while applying a negative potential. Flow of liquid through the flow channel is rapidly switched from preconditioning solution to a target solution containing an organic target solute to be measured. The transient response of the system resulting from exposure of the working electrode to organic target solute is detected by measuring current density during an initial transient time period. An unknown concentration of target solute is determined by comparing the transient response with one or more transient responses characteristic of known concentrations. A preferred measuring system is operable to switch flow from preconditioning solution to target solution in about 200 milliseconds or less.

23 Claims, 17 Drawing Sheets

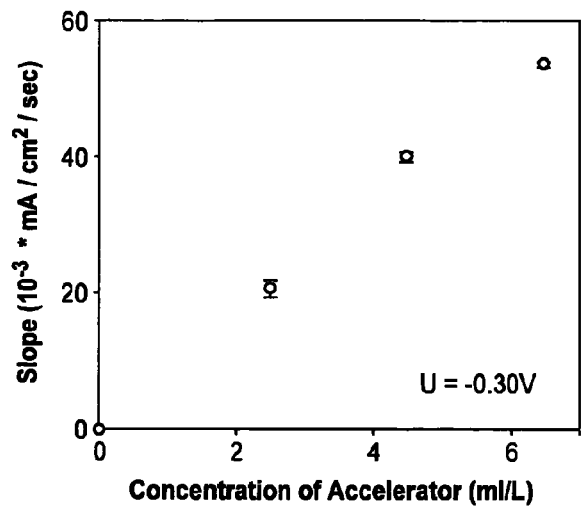
FIG. 7
FIG. 8
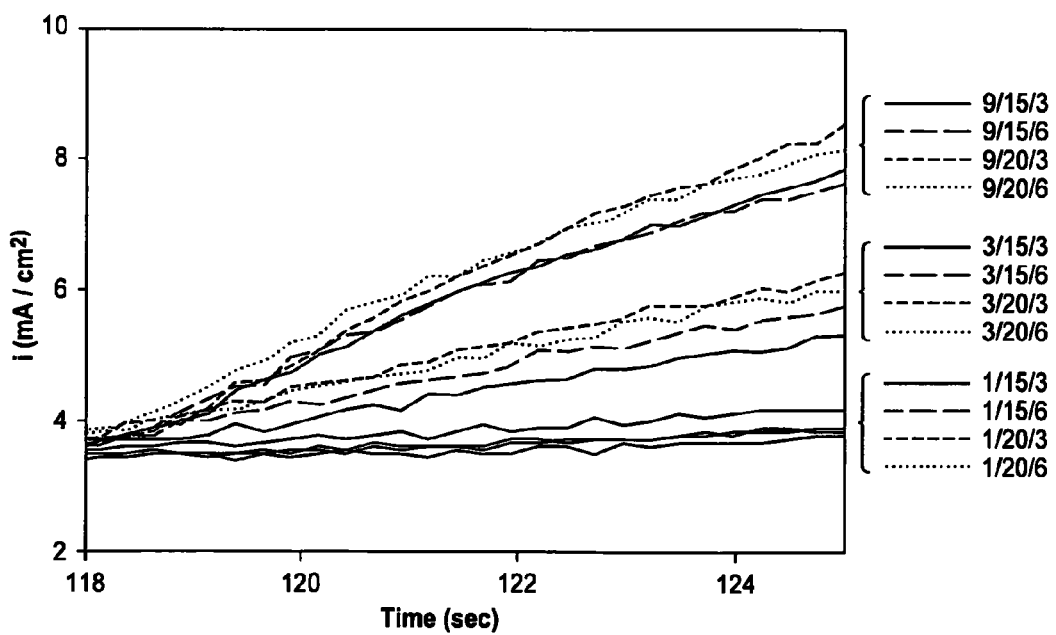

MONITORING OF ELECTROPLATING ADDITIVES

FIELD OF THE INVENTION

The present invention pertains to the field of integrated circuit fabrication, particularly to systems and methods for measuring and monitoring concentrations of organic additives in electroplating solutions.

BACKGROUND OF THE INVENTION

Integrated circuits are formed on wafers by well-known processes and materials. These processes typically include the deposition of thin film layers by sputtering, metal-organic decomposition, chemical vapor deposition, plasma vapor deposition, and other techniques. These layers are processed by a variety of well-known etching technologies and subsequent deposition steps to provide a completed integrated circuit.

A crucial component of integrated circuits is the wiring or metallization layer that interconnects the individual circuits. Conventional metal deposition techniques include physical vapor deposition (e.g., sputtering and evaporation) and chemical vapor deposition techniques. Integrated circuit manufacturers have also developed electrolytic and electroless plating techniques to deposit primary conductor films on semiconductor substrates.

Wiring layers traditionally contained aluminum and a plurality of other metal layers that are compatible with aluminum. Around 1997, new technology facilitated a transition from aluminum to copper wiring layers. This technology demanded corresponding changes in process architecture towards damascene and dual damascene architecture, as well as new process technologies.

Copper damascene and dual damascene circuits are produced by initially forming trenches and other embedded features in a wafer, as needed for circuit architecture. These trenches and embedded features are formed by conventional photolithographic processes in a nonconductive substrate, such as a silicon oxide. Usually, a barrier layer, for example, of silicon nitride or tantalum, is deposited next. An initial seed or strike layer, (e.g., a copper or ruthenium layer having a thickness of about 5 nanometers (nm) to 200 nm) is then deposited by a conventional physical or vapor deposition technique. The seed layer is used as a base layer to conduct current for electroplating thicker films. Thinner seed layers are preferred to reduce overhang and closure of very small features by metal from the seed layer. The seed layer functions as the initial cathode of an electroplating cell. Electrical contacts to the wafer are normally made at its edge.

In electroplating processes, it is generally desirable to control the thickness profile of the deposited metal to be as uniform as possible. A uniform profile is advantageous in subsequent etchback or polish removal steps, as well as in uniform void-free filling of vias and trenches. Prior art electroplating techniques are susceptible to thickness irregularities. Factors contributing to these irregularities include the size and shape of the electroplating cell, electrolyte depletion effects, hot edge effects, and the terminal effect.

A conventional electroplating bath typically contains the metal to be plated together with associated anions in an acidic solution. Copper electroplating is usually performed using $CuSO_4$ and a chloride dissolved in an aqueous solution of sulfuric acid. In DC electroplating, additives such as accelerators, suppressors, and levelers are typically included in the electrolytic plating solution to improve electroplating behavior by, among others, enhancing chemical reactions, improving surface deposition, improving thickness uniformity, and enhancing filling of high aspect ratio features. Sulfuric acid provides high conductivity to the electrolyte, and chloride ions enhance additive performance.

Three types of electroplating bath additives are in common use, subject to design choice by those skilled in the art. A suppressor additive is used to decrease the current density, and thus the deposition rate on the surface of the wafer at a given applied voltage. This allows differentiation in deposition rate between the wafer surface and the inside of high aspect ratio features, thereby enhancing the void-free fill of high aspect ratio features. Typical suppressors are large molecules, typically having an average molecular weight (MW) in a range of about from 2,000 to 6,000 that increase the surface polarization layer and prevent copper ion from readily adsorbing onto the surface. Thus, suppressors function as blockers. Suppressors cause the resistance of the surface to be very high in relation to the electroplating bath. Trace levels of chloride or other ion may be required for suppressors to be effective.

Accelerator additives accumulate within the high aspect ratio features to increase the local current density relative to the suppressed field and thus aid in void free filling. Accelerator additives are normally catalysts that accelerate the plating reaction. Accelerators typically are rather small molecules (e.g., 300 MW) that normally contain sulfur, and they need not be ionic. Accelerators adsorb onto the surface and increase the flow of current. Accelerators may occur not as the species directly added to the electroplating bath, but as breakdown products of such molecules. In either case, the net effect of accelerators is to increase current flow and accelerate the reaction when such species are present or become present through chemical breakdown.

A leveler additive is present to improve overall deposit planarity and increase the ease of subsequent CMP processing. Levelers behave like suppressors, but tend to be more electrochemically active (i.e., are more easily electrochemically transformed) than suppressors. Levelers are typically consumed during electroplating. Levelers tend to supress plating on raised regions of the surface undergoing plating, thus, tending to level the plated surface.

In conventional electroplating solutions, the additive components are designed to provide ideal characteristics for bottom-up fill of trenches and vias, as well as planarization of plating above filled features. Organic additives are present in an electroplating solution in low concentrations, usually measured in parts per million (ppm). The low concentrations of organic additives must be closely controlled to achieve desired deposition behavior and desired properties of deposited metal.

Cyclic voltammetric stripping (CVS) is a widely used method for monitoring and controlling plating bath additives. CVS involves cycling the potential of an inert electrode (e.g., Pt) in a cleaning solution between fixed potential limits so that metal is ultimately plated onto the electrode and then stripped from the electrode surface. The cycling of potential is designed to establish a steady state for the electrode surface so that reproducible results are obtained. Accumulation of organic films or other contaminants on the electrode surface is avoided by periodically cycling the potential of the electrode in a plating solution without organic additives and, if necessary, polishing the electrode. Cyclic pulse voltammetric stripping (CPVS), also known as cyclic step voltammetric stripping (CSVS), is a variation of the CVS method that employs discrete changes in potential during the analysis to condition the electrode to improve measurement precision. A rotating disk electrode is typically employed for both CVS and CPVS analysis to provide controlled hydrodynamic conditions. A limitation of techniques using a rotating disk electrode is that the solution studied cannot be changed while a measurement is being completed.

In CVS and CPVS analyses, a metal deposition rate is determined from the current or charge passed during metal electrodeposition. Typically, the charge associated with anodic stripping of the metal from the electrode is measured. Various techniques involving cyclic voltammetry are described in U.S. Pat. No. 7,186,326, issued Mar. 6, 2007, and U.S. Pat. No. 7,270,733, issued Sep. 18, 2007, which are hereby incorporated by reference. Other less common techniques for monitoring the concentration of organic additives in electroplating solutions that do not involve CVS are described briefly in U.S. Pat. No. 7,270,733.

Currently used techniques for monitoring the concentration of organic additives are typically characterized by one or more of the following shortcomings. A common problem is the large size and large footprint associated with detection and analysis equipment. Another problem is the large amount of reagents used in analysis, and the corresponding high expense. Additionally, some techniques have demanding equipment requirements; for example, some techniques use expensive and unreliable syringe pumps, while others use complex frequency response locks in amplifiers and power supplies. Some techniques are suitable for measuring one type of organic additives, but are less suitable or unsuitable for measuring other types of organic additives. Further, commonly used techniques generally require complicated calibration and analysis. More importantly, the accuracy, precision and reliability of the measurements of some commonly used monitoring devices are often unsatisfactory.

Therefore, there is a need, particularly in the field of integrated circuit fabrication, for systems and methods useful for monitoring and controlling the concentrations of organic additives in electroplating solutions.

SUMMARY OF THE INVENTION

The present invention helps to solve some of the problems outlined above by providing methods and systems for monitoring the concentrations of organic plating additives in copper electroplating solutions used for bottom-up filling of high-aspect ratio features. Embodiments in accordance with the invention require only small volumes of plating bath solution to measure the concentration of plating additive. A complete concentration measurement of a single additive is typically accomplished within about five minutes, and the same equipment can be used to measure concentrations of different additives. For example, the concentrations of additive, suppressor and leveler in a plating bath can all be measured with the same piece of equipment in 10 or 15 minutes. Furthermore, concentration measurements in accordance with the invention are accurate across broad ranges of additive concentrations; that is, the accuracy of a concentration measurement for a particular additive is not substantially influenced by different concentrations of other additives in an electroplating bath. A measuring system in accordance with the invention can be assembled in a small volume having a small footprint.

The invention is described herein mainly with reference to the electroplating of thin copper films on 300 mm integrated circuit wafers. It is understood, however, that methods and systems in accordance with the invention are also useful for any process requiring the monitoring of organic solutes in a process solution.

A basic embodiment of a method in accordance with the invention for ascertaining the concentration of a target solute in an electrolytic solution comprises steps of: (a) flowing an electrolytic preconditioning solution containing metal ions and a preconditioning species through a flow channel of a flow-through electrolytic meter; (b) causing deposited metal and adsorbed preconditioning species to form on a working electrode located in the flow channel by applying a potential to the working electrode; (c) then ceasing flow of the preconditioning solution through the flow channel; (d) immediately after ceasing flow of preconditioning solution, initiating flow of an electrolytic target solution through the flow channel, the electrolytic target solution including metal ions and a target concentration of the target solute; (e) during a transient time period immediately after initiating flow, applying a potential to the working electrode and measuring a plurality of transient values of an electrical property of the electrolytic target solution using the flow-through electrolytic meter, wherein the transient values are influenced by a presence of the adsorbed preconditioning species; and (e determining the target concentration from the plurality of transient values measured during the transient time period. In some embodiments, the electrical property being measured is current density; that is, a constant electrical potential is applied to the working electrode so that changing transient values of current density are measured. In some embodiments, the electrical property being measured is voltage (or electrical potential); that is, a constant current density is maintained between the working electrode and the counter electrode in the flow-through electrolytic cell and changing transient values of voltage are measured.

Methods in accordance with the invention generally do not involve stripping the deposited metal and the adsorbed preconditioning species prior to initiating flow of electrolytic target solution and prior to the transient time period. Furthermore, in contrast to techniques of the prior art referred to as cyclic voltammetric stripping (CVS) and to related techniques, methods in accordance with the invention do not involve stripping deposited metal or measuring the amount of deposited metal. Therefore, in typical embodiments in accordance with the invention, measuring transient values in step (e) above does not require measuring a rate of metal plating or a rate of metal etching at the working electrode.

In some embodiments in accordance with the invention, determining the target concentration from the plurality of transient values comprises calculating a target transient rate constant using the transient values, wherein the target transient rate constant expresses approximately a rate of change in the transient values as a function of time during the transient time period. In some embodiments, determining the target concentration from the plurality of transient values further comprises ascertaining the target concentration of the target solute in the target solution by comparing the target transient rate constant with one or more standard transient rate constants corresponding to known concentrations of the target solute. In some embodiments, an interaction of the target solute with the preconditioning species during the transient time period affects the transient values of the electrical property.

Some embodiments further comprise mixing a bath solution containing the target solute with a base liquid to form the electrolytic target solution before step (d) above. In some of these embodiments mixing dilutes a concentration of preconditioning species in the bath solution.

Some embodiments further comprise, before the step (d) above, adding an activator species to a bath solution containing a target solute precursor to form the target solute.

In some embodiments, ceasing flow of preconditioning solution in step (c) and initiating flow of electrolytic target solution in step (d) comprise switching liquid flow to the working electrode in the flow channel from the preconditioning liquid to the electrolytic target solution within a switching time not exceeding 500 milliseconds. In some embodiments, ceasing flow of preconditioning solution in step (c) and initiating flow of electrolytic target solution in step (d) comprise switching liquid flow through a flow valve from a preconditioning liquid to an electrolytic test solution, wherein the flow valve comprises a first inlet port, a second inlet port and an outlet port, and the outlet port is fluidically connected to the flow channel of the flow-through electrolytic meter.

In some embodiments, the preconditioning species comprises an organic plating suppressor; and the target solute comprises an organic plating accelerator. In some embodiments, the electrolytic preconditioning solution comprises functional suppressor species consisting essentially of polyethylene glycol (PEG) polymers and polypropylene glycol (PPG) polymers (or their block copolymers) having an average molecular weight in a range of about from 1500 to 3500, at a molar ratio of PPG to PEG, PPG:PPE, in a range of about from 0.2 to 0.8, and the organic plating accelerator comprises a functional species consisting essentially of bis-(3-sulfopropyl)-disulfide (SPS). In some embodiments, the electrolytic preconditioning solution has a concentration of the functional suppressor species of PPG and PEG in a range of about from 50 ppm to 1500 ppm, and initiating flow of electrolytic target solution in step (d) comprises flowing a target solution comprising bis-(3-sulfopropyl)-disulfide (SPS) at a concentration in a range of about from (10 ppm to 100 ppm)/2. Some of these embodiments further comprise, before step (d) above, mixing an electrolytic plating bath solution from an electrolytic plating bath with a base liquid to form the electrolytic target solution. The base liquid consists essentially of virgin electrolytic plating solution having substantially no organic plating additives. In some embodiments, mixing dilutes concentrations of solutes of the electrolytic plating bath solution by a factor of about two.

In some embodiments, the preconditioning species comprises a chloride ion, the electrolytic preconditioning solution is substantially free of organic plating additives, and the target solute consists essentially of an organic plating suppressor. In some embodiments, the preconditioning species comprises chloride ion (Cl$^-$), and the target solute comprises functional suppressor species consisting essentially of polyethylene glycol (PEG) polymers and polypropylene glycol (PPG) polymers (or their block copolymers) having an average molecular weight in a range of about from 1500 to 3500, at a molar ratio of PPG to PEG, PPG:PPE, in a range of about from 0.2 to 0.8. In some embodiments, the electrolytic preconditioning solution has a chloride ion concentration in a range of about from (10 ppm to 500 ppm), and initiating flow of electrolytic target solution in step (d) comprises flowing a target solution comprising a concentration of the functional suppressor species of PPG and PEG at a concentration in a range of about from (50 ppm to 600 ppm)/32. Some embodiments further comprise, before step (d) above, mixing an electrolytic plating bath solution from an electrolytic plating bath with a base liquid to form the electrolytic target solution, wherein the base liquid consists essentially of virgin electrolytic plating solution having substantially no organic plating additives. In some embodiments, mixing dilutes concentrations of solutes in the electrolytic plating bath solution by a factor of about thirty-two.

In some embodiments, the preconditioning species comprises an organic plating accelerator, and the target solute consists essentially of an organic plating leveler. In some of these embodiments, the preconditioning species further comprises an organic plating suppressor. In some embodiments, the preconditioning species, comprises an organic plating accelerator comprising a functional species consisting essentially of bis-(3-sulfopropyl)-disulfide (SPS), and further comprises functional suppressor species consisting essentially of polyethylene glycol (PEG) polymers and polypropylene glycol (PPG) polymers (or their block copolymers) having an average molecular weight in a range of about from 1500 to 3500, at a molar ratio of PPG to PEG, PPG:PPE, in a range of about from 0.2 to 0.8; and the target solute comprises an organic leveler comprising functional species poly(vinyl pyrrolidone (PVP) having an average molecular weight in a range of about from 3,000/4 to 5,000/4. In some embodiments, the electrolytic preconditioning solution comprises plating accelerator comprising a functional species consisting essentially of bis-(3-sulfopropyl)-disulfide (SPS) at a concentration in a range of about from 30 ppm to 400 ppm, and further comprises a concentration of the functional suppressor species of PPG and PEG in a range of about from 25 ppm to 200 ppm.

Some embodiments of a method in accordance with the invention further comprise: before step (d) above, mixing an electrolytic plating bath solution from an electrolytic plating bath with a base liquid to form the electrolytic target solution; wherein the base liquid consists essentially of virgin electrolytic plating solution having substantially no organic plating additives. In some embodiments, mixing dilutes concentrations of solutes of the electrolytic plating bath solution by a factor of about four.

A basic embodiment of a system in accordance with the invention for measuring the concentration of a target solute in an electrolytic solution comprises: a flow-through electrolytic meter; a first inlet conduit; a second inlet conduit; and a switching valve. The flow-through electrolytic meter includes a flow channel, a working electrode located in the flow channel, and a counter electrode located in the flow channel. The flow-through electrolytic meter is operable to measure transient values of an electrical property of an electrolytic solution flowing through the flow channel. The switching valve is connectable to the first inlet conduit, the second inlet conduit, and the flow channel of the flow-through electrolytic meter. The switching valve is operable to switch liquid flow into the flow channel from the first inlet conduit to the second inlet conduit at a switching time not exceeding 1000 milliseconds. In exemplary embodiments, the flow channel comprises a length dimension in a range of about from 1 cm to 3 cm, a height dimension in a range of about from 100 μm to 1.0 cm, and a width dimension in a range of about from 0.3 cm to 2.0 cm. In some embodiments, the working electrode surface is substantially flat, is substantially flush with a flow channel wall surface, and comprises a working electrode surface area in a range of about from 0.01 cm$^2$ to 0.05 cm$^2$. In some embodiments, the working electrode is located in a range of about from 0.5 cm to 2.0 cm downstream from the channel entrance. Generally, the counter electrode surface is substantially flat, comprises a counter electrode surface area in a range of about from 0.03 cm$^2$ to 0.20 cm$^2$, is substantially flush with a flow channel wall surface in substantially the same plane as the working electrode surface, and is located in a range of about from 0.10 cm to 0.40 cm downstream from the working electrode surface.

Some embodiments of a system in accordance with the invention further comprise: a preconditioning liquid subsystem for providing a preconditioning liquid stream, the preconditioning liquid subsystem being fluidically connectable to the first inlet conduit; and a test solution subsystem for providing an electrolytic test solution stream, the test solution subsystem being fluidically connectable to the second inlet conduit. In some embodiments, the preconditioning liquid subsystem further comprises: a preconditioner mixer for mixing a preconditioner and a base liquid to make a preconditioning liquid. Typically, the preconditioner mixer is fluidically connectable to a preconditioner source, to a base liquid source, and to the first inlet conduit. In some embodiments, the test solution subsystem is operable to dilute an electrolytic bath solution from an electrolytic bath in the test solution mixer with a base liquid comprising an electrolytic plating solution. In some embodiments: the base liquid source includes the base liquid, the base liquid comprising an electrolytic plating solution without significant amounts of organic plating additives; the electrolytic bath includes an electrolytic plating bath comprising an electrolytic plating solution including one or more organic plating additives including the target solute; and the electrolytic test liquid comprises an electrolytic solution containing the one or more organic plating additives including the target solute. In some embodiments, the test solution subsystem is operable to dilute the electrolytic bath solution from the electrolytic plating bath in the test liquid mixer using the base liquid to generate the electrolytic test solution.

Other features, characteristics and advantages of embodiments in accordance with the invention will become apparent in the detailed description below.

BRIEF DESCRIPTION OF THE DRAWINGS

FIG. 7 contains a graph in which the mean slope of the transient rate of change of current density per second (converted to positive values) is plotted with standard deviation bars as a function of accelerator concentration in diluted target solutions;

FIG. 8 contains a graph in which current density responsive to accelerator is plotted as a function of time;

DETAILED DESCRIPTION OF THE INVENTION

Figure 1A:
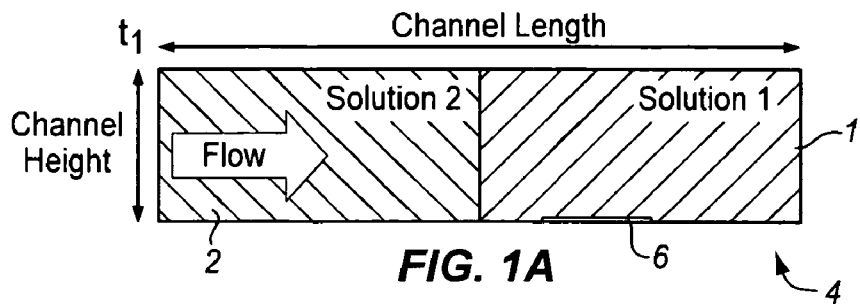
FIGS. 1A-1C depict the transition of two solutions over a working electrode in a flow-through channel.

The invention is described herein with reference to FIGS. 1-23. It should be understood that the structures and systems depicted in schematic form in FIGS. 1-4, 21 and 23 are used to explain the invention and are not precise depictions of actual structures and systems in accordance with the invention. Similarly, methods in accordance with the invention described with reference to the process flow sheets contained in FIGS. 6, 11, 15 and 20 are exemplary. Similarly, the systems and methods described in Examples 1-9 below are exemplary. Some methods in accordance with the invention include additional steps and steps performed in somewhat different sequences from those described herein. For the sake of clarity, parts and elements of various embodiments having similar structure and function are identified using the same reference numerals in the figures below. Methods in accordance with the invention are described herein mainly with reference to electrolytic plating solutions and the measurement of concentrations of organic additives in plating solutions. It is understood that methods in accordance with the invention are also generally useful for measuring and monitoring the concentration of one or more organic solutes in electrolytic solution. Methods in accordance with the invention are described herein mainly with reference to applying a substantially constant electric potential to a working electrode in a flow-through electrolytic cell and measuring changes in current density. One of ordinary skill in the art will understand that substantially the same techniques may be applied in accordance with the invention by generating a substantially constant current density in the electrolytic cell and then measuring changes in voltage. Furthermore, the embodiments described herein are not intended to limit the scope of the invention, which is defined in the claims below.

Figure 1B:
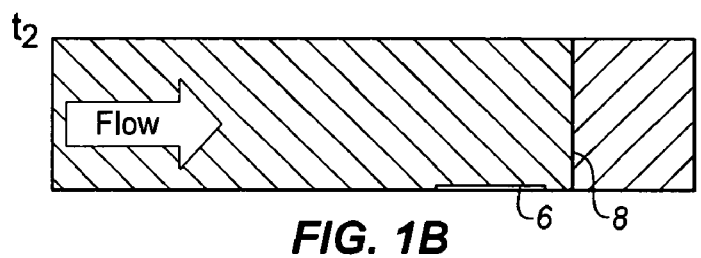
Figure 1C:
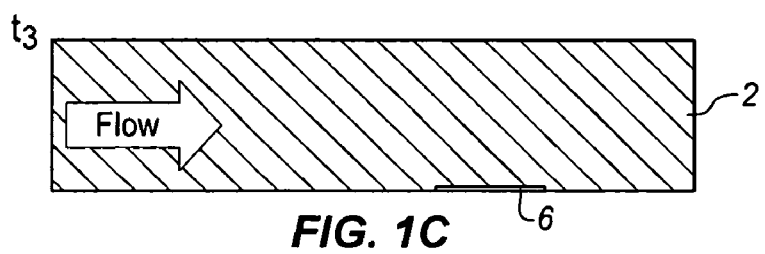
Figure 1D:
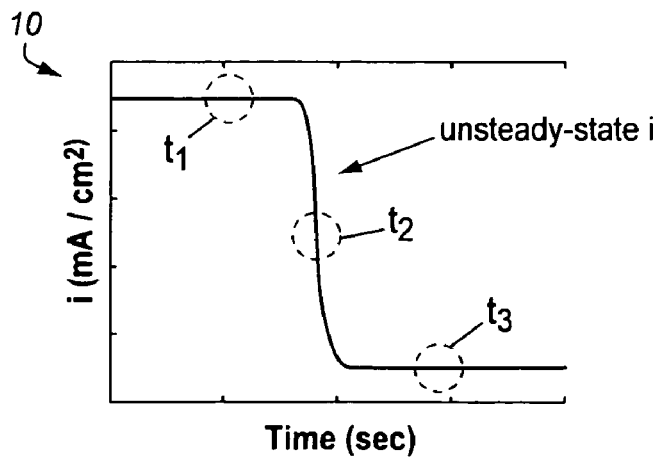
FIG. 1D contains a representative graph of measured current density plotted as a function of time.

An adsorption/desorption (ADDE) chemical monitoring system (CMS) utilizes the transitioning between flow of two liquids over a working electrode in a flow-through electrolytic meter. FIG. 1 depicts the transition of two solutions over working electrode in a flow-through channel. FIG. 1A depicts the locations of solution 1 and solution 2 in flow-through channel 4 at a first time, $t_1$. At time $t_1$, solution 1 is above working electrode 6 and solution 2 has not yet reached working electrode 6. FIG. 1B depicts the locations of solution 1 and solution 2 in flow-through channel 4 at a second time, $t_2$, after time $t_1$. At time $t_2$, the interface 8 between solution 1 and solution 2 has moved downstream beyond working electrode 6 so that only solution 2 is above working electrode 6. FIG. 1C depicts the locations of solution 1 and solution 2 in flow-through channel 4 at a third time, $t_3$, after time $t_2$. At time $t_3$, the interface (not shown) between solution 1 and solution 2 has moved further downstream beyond working electrode 6 so that working electrode 6 has been exposed only to solution 2 between times $t_2$ and $t_3$. FIG. 1D contains a representative graph 10 in which current density measured using working electrode 6 is plotted as a function of time. Graph 10 illustrates the change in measured current densities between a first steady-state current density at time $t_1$ and the second steady-state current density at time $t_3$. Graph 10 also illustrates the unsteady-state values of current during a transition time, which includes time $t_2$, which began substantially immediately upon liquid interface 8 in liquid flow channel 4 reaching working electrode 6. The transition time ended when measured current density approached the new steady-state value shown at time $t_3$.

This specification contains language referring to "adsorption" and "desorption" of one or more chemical species, e.g., organic plating additives, to the surface of a working electrode during measurement operations. The exact mechanisms of behavior of organic plating additives during metal deposition are generally not known with certainty, and the behavior of different species at the surface of an electrode also vary. The term adsorption is sometimes used in a narrow sense to mean that a chemical species attaches to a surface. In this specification, the term adsorption includes its narrow meaning of attachment of the species to a surface, but also includes a broader meaning of the term that includes accumulation of a species at or proximate to a working electrode surface, but not necessarily attached to the surface. The term desorption as used in this specification has a similarly broad meaning that is essentially the opposite of adsorption; that is, desorption means a release from a surface or migration away from a region proximate to the surface. As used in this specification, the term desorption also includes an even broader meaning that refers to a dissipation or deactivation of the influence of a chemical species at a surface, particularly at the surface of a working electrode. For example, without being bound to any particular theory, dissipation or deactivation of the influence of a chemical species might arise from incorporation of the species into a surface layer, as well as from a release of the species or its migration away from the surface.

One of ordinary skill in the art will recognize that the precise chemical composition of a solute changes in solution, particularly during electrochemical action. Accordingly, terms such as "preconditioning species", "target solute" and other terms identifying particular chemical species in this specification refer not only to the chemical species as added to a solution but also to related forms resulting from phenomena such as dissolution, breakdown and activation.

The terms "measure", "measurement" and related terms are used in this specification to refer both to direct measurements and indirect measurements. An example of a relatively direct measurement is the measurement of current density at a given time in accordance with the invention using a flow-through electrolytic cell and a potentiostat. An example of an indirect measurement is measurement of an additive concentration by collecting transient values of current density, using the transient values to calculate a transient rate constant, and comparing the calculated rate constant with standard rate constants to determine an unknown concentration. The meaning of the term in a particular instance is clear from its context.

In this specification, the term "transient response", "unsteady state response" and related terms refer to the changes in current density (or other measured electrical property) over time during a relatively short "transient time" period as a result of the working electrode being exposed to a target solute in an electrolytic solution. The term "steady state response" and related terms refer to the substantially constant value of current density (or other measured electrical property) over time during a preconditioning phase as a result of a working electrode being exposed to an electrolytic solution containing preconditioning species, or towards the end of a target measurement phase. The meaning of the term "response" is clear from the context in which it is used.

Example 1

Figures 2A, 2B:
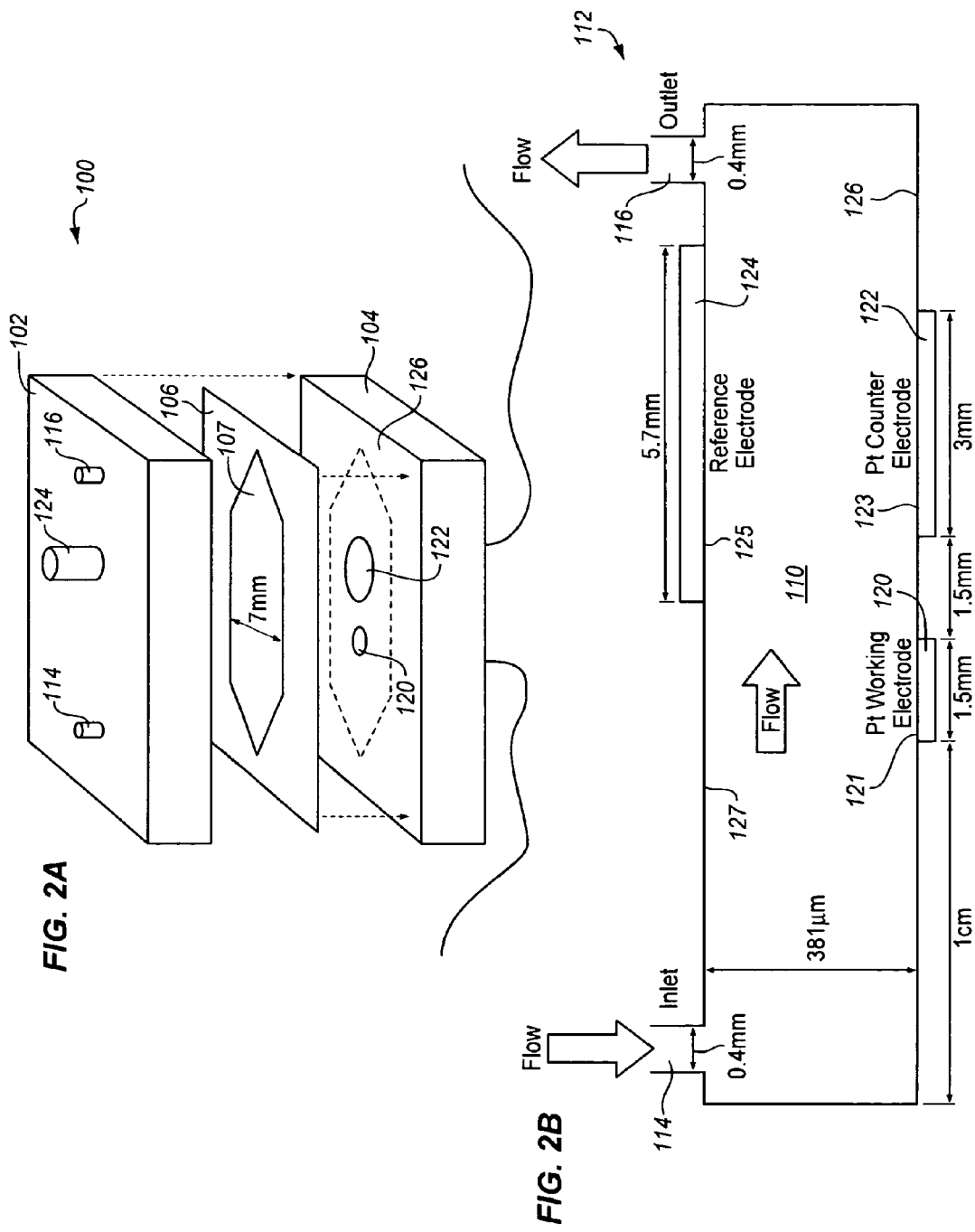
FIGS. 2A and 2B depict schematically an exemplary flow-through electrolytic detection cell in accordance with the invention.

FIGS. 2A and 2B depict an exemplary flow-through cell 100 in accordance with the invention. FIG. 2A depicts schematically an expanded perspective view of flow-through cell 100 having top plate 102 and bottom plate 104. Plates 102, 104 are typically made from plastic or other electrically non-conductive material. Flow-through cell 100 also includes electrically non-conductive gasket 106 located between top plate 102 and bottom plate 104. When flow-through cell 100 is assembled (not shown in FIG. 2A), cut-out area 107 in gasket 106, together with top plate 102 and bottom plate 104, serves to define a flow channel 110, depicted schematically in cross-sectional view 112 in FIG. 2B. As depicted FIGS. 2A and 2B, a flow-through cell 100 further includes channel inlet port 114, channel outlet port 116, working electrode 120 having top surface 121, counter electrode 122 having top surface 123, and reference electrode 124 having bottom surface 125. In the exemplary embodiment, channel inlet port 114 and channel outlet port 116 each have a diameter of 0.4 mm and are located as close to the respective ends of the flow-through channel as possible in order to eliminate dead spots of fluid flow. The location of the ports on the top or bottom of the channel is not important. In the exemplary embodiment, working electrode 120 and counter electrode 122 substantially comprise platinum, and reference electrode 124 is either a silver/silver-chloride electrode or a mercury/mercury-sulfate electrode, as known and used in the art. In the exemplary embodiment, working electrode 120 is round and has a diameter of 0.15 centimeters (cm), and counter electrode 122 is round and has a diameter of 0.3 cm. Gasket 106 has a thickness of approximately 381 micrometers (μm) when pressed between bottom plate 104 and top plate 102 in assembled flow-through cell 100. Accordingly, flow-through channel 110 has a height of about 381 μm, as depicted in FIG. 2B. Flow channel 110 has a total length (horizontal dimension in FIG. 2B) of approximately 2 cm, and a width (not shown) of approximately 0.7 cm. As depicted in FIG. 2B, working electrode 120 is located about 1 cm from the inlet of flow channel 110 and counter electrode 122 is located about 1.5 millimeters (mm) downstream from working electrode 120. As depicted in FIG. 2A, cut-out area 107 and accordingly flow channel 110 preferably are tapered at the inlet and outlet ends so that "dead" zones of fluid do not develop proximate to the inlet and outlet ends in flow channel 110. Working electrode 120 and counter electrode 122 are located on the same side of flow channel 110 and their top surfaces 121, 123 are substantially flush with flow channel bottom 126 defined by bottom plate 104. Reference electrode 124 is located at the top of flow channel 110, that is, on the opposite side of flow channel 110 from electrodes 120, 122. Bottom surface 125 of reference electrode 124 is substantially flush with the top 127 of flow channel 110 defined by top plate 102. Design of the electrodes flush with the surfaces of flow channel 110 enhances undisturbed flow of fluid through the channel and reduces the collection of air bubbles in the cell, which would disturb measurements. Electrodes 120, 122 and 124 are connected to the potentiostat (not shown) through shielded cable to reduce the influence of electrical noise from other parts of the measuring apparatus or plating tool on the relatively low currents (e.g., less than 4 milliamps) measured by the potentiostat. A flow-through electrolytic cell 100 with the potentiostat is useful together with peripheral equipment known in the art (e.g., power supply, electronic recording instruments, computer) in a flow-through electrolytic meter in accordance with the invention to measure current and electrical potential (voltage) as a function of time. Flow channel 110 of exemplary flow-through cell 100 has a volume of approximately 0.06 cm$^3$, which allows a concentration measurement in accordance with the invention using a liquid volume of only about 5 milliliters (mL) pumped through the flow channel.

Exemplary dimensions of a flow channel in a flow-through cell in accordance with the invention include: a length dimension in a range of about from 1 cm to 3 cm, a height dimension in a range of about from 100 μm to 1.0 cm, and a width dimension in a range of about from 0.3 cm to 2.0 cm. Accordingly, a flow channel in a flow-through cell in accordance with the invention generally has a volume in a range of about from $3 \times 10^{-3}$ cm$^3$ to 6 cm$^3$, more typically in a range of about from $3 \times 10^{-3}$ cm$^3$ to 0.6 cm$^3$. Generally, a working electrode surface is substantially flat, is substantially flush with a flow channel wall surface, comprises a working electrode surface area in a range of about from 0.01 cm$^2$ to 0.05 cm$^2$, and is located in a range of about from 0.5 cm to 2.0 cm downstream from a channel entrance. Generally, a counter electrode surface is substantially flat, comprises a counter electrode surface area in a range of about from 0.03 cm$^2$ to 0.20 cm$^2$, is substantially flush with a flow channel wall surface in substantially the same plane as the working electrode surface, and is located in a range of about from 0.10 cm to 0.40 cm downstream from the working electrode surface.

Figure 3:
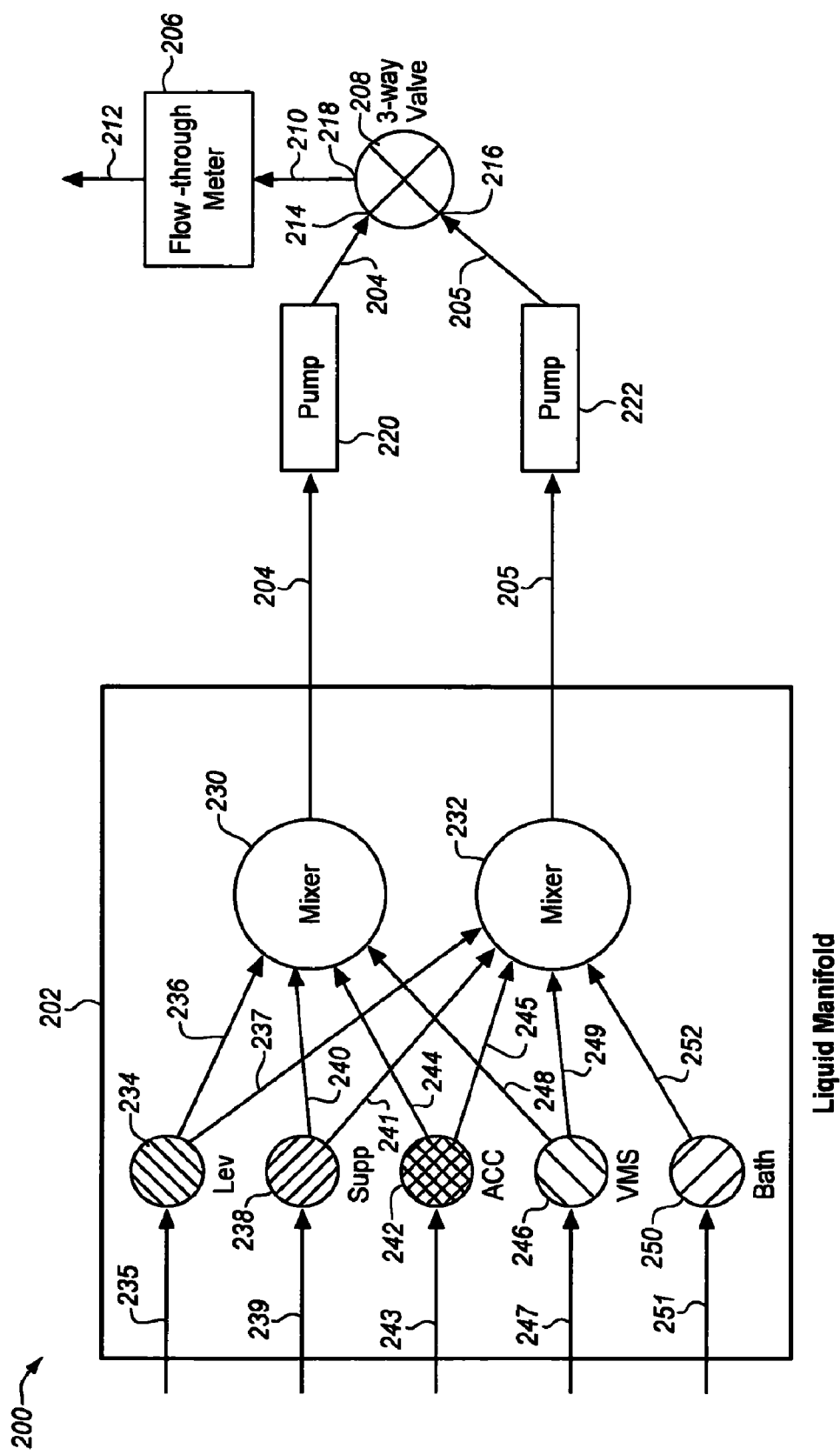
FIG. 3 depicts schematically a concentration measuring system in accordance with the invention.

FIG. 3 depicts schematically a concentration measuring system 200 in accordance with the invention. Measuring system 200 comprises liquid mixing manifold 202 connected to a first inlet conduit 204 and a second inlet conduit 205. Measuring system 200 further comprises flow-through meter 206, which includes a flow channel (e.g., a flow channel 110 as described above) and a potentiostat. Measuring system 200 also comprises valve 208, channel inlet line 210 and channel outlet line 212. Valve 208 includes a first valve inlet 214, a second valve inlet 216 and a valve outlet 218, connected to channel inlet line 210. First inlet conduit 204 is connected to first valve inlet 214, and a second inlet conduit 205 is connected to second valve inlet 216. Switching valve 208 is operable to switch liquid flowing through channel inlet line 210 into flow-through meter 206 from liquid flowing in first inlet conduit 204 to liquid flowing in second inlet conduit 205. A pump 220 located in first inlet conduit 204 serves to pump electrolytic preconditioning solution from manifold 202 to valve inlet 214. A pump 222 located in second inlet conduit 205 serves to pump electrolytic target solution from manifold 202 to valve inlet 216. In preferred embodiments, switching valve 208 is operable to switch liquid flow through channel inlet line 210 into the flow channel of flow-through meter 206 from liquid flowing in first inlet conduit 204 to liquid flowing in second inlet conduit 205 within a switching time not exceeding one second. Preferably, switching time does not exceed 500 ms. In more preferred embodiments, the switching time does not exceed 200 ms, and in even more preferred embodiments, the switching time does not exceed 100 ms.

Liquid mixing manifold 202 comprises preconditioner mixer 230 and target mixer 232. Liquid mixing manifold 202 includes leveler valve 234 connected to leveler source line 235, which conducts plating leveler solution from a leveler source (not shown) to a valve inlet of leveler valve 234. Leveler valve 234 is also connected to leveler distribution lines 236, 237. Leveler distribution line 236 conducts leveler solution from leveler valve 234 into preconditioner mixer 230, and leveler distribution line 237 conducts leveler solution from leveler valve 234 into target mixer 232. Liquid mixing manifold 202 includes suppressor valve 238 connected to suppressor source line 239, which conducts plating suppressor solution from a suppressor source (not shown) to a valve inlet of suppressor valve 238. Suppressor valve 238 is also connected to suppressor distribution lines 240, 241. Suppressor distribution line 240 conducts suppressor solution from suppressor valve 238 into preconditioner mixer 230, and suppressor distribution line 241 conducts suppressor solution from suppressor valve 238 into target mixer 232. Liquid mixing manifold 202 includes accelerator valve 242 connected to accelerator source line 243, which conducts plating accelerator solution from an accelerator source (not shown) to a valve inlet of accelerator valve 242. Accelerator valve 242 is also connected to accelerator distribution lines 244, 245. Accelerator distribution line 244 conducts accelerator solution from accelerator valve 242 into preconditioner mixer 230, and accelerator distribution line 245 conducts accelerator solution from accelerator valve 242 into target mixer 232. Liquid mixing manifold 202 includes VMS valve 246 connected to VMS source line 247, which conducts virgin make-up solution (VMS) from a VMS source (not shown) to a valve inlet of VMS valve 246. VMS valve 246 is also connected to VMS distribution lines 248, 249. VMS distribution line 248 conducts VMS solution from VMS valve 246 into preconditioner mixer 230, and VMS distribution line 249 conducts VMS solution from VMS valve 246 into target mixer 232. Liquid mixing manifold 202 includes bath valve 250 connected to bath line 251, which conducts target solution from a source of target solution (e.g., an electroplating bath, not shown) to a valve inlet of bath valve 250. Bath valve 250 is also connected to bath distribution line 252. Bath distribution line 251 conducts target solution from bath valve 250 into target mixer 232. System 200 is operable to make test target solutions with known concentrations of target solutes. System 200 is also operable to make preconditioning solutions used in measurement processes in accordance with the invention. System 200 is also operable to mix about solution with VMS to dilute the concentration of additives in the final target solution, as explained in more detail further below. In some embodiments, bath line 251 is connectable directly or indirectly with one or more sources of electrolytic solution containing a known concentration of target solute used for calibrating the flow-through electrolytic meter, as well as being connectable to a bath containing a target solution containing an unknown concentration of target solute. Some preferred embodiments include a cleaning solution source and a pump for pumping oxidizing cleaning solution through a measuring apparatus, in particular through the flow channel of a flow-through electrolytic cell.

Generally, an ADDE method in accordance with the invention includes a preconditioning phase and a target measuring phase. During the preconditioning phase, an electrolytic preconditioning solution containing metal ions and a least one preconditioning species flows through the flow channel (e.g., flow channel 110) of a flow-through electrolytic meter in accordance with the invention. The preconditioning solution contains substantially no target solute. A negative potential applied to the working electrode in the flow channel causes metal deposition and adsorption of preconditioning species on the working electrode. Generally, the preconditioning phase is conducted by flowing preconditioning solution through the flow channel for at least about 30 seconds, typically in a range of about from one minute to three minutes. Then, the preconditioning phase ends by ceasing the flow of preconditioning solution to the flow channel. Immediately after ceasing the flow of preconditioning solution through the flow channel, the target measurement phase begins by initiating flow of electrolytic target solution through the flow channel. The electrolytic target solution includes metal ions and a target concentration of target solute. Generally, the target concentration is either a known concentration used to calibrate the flow-through electrolytic meter, or an unknown concentration to be measured using the electrolytic meter. Generally, the switching time for switching flow through the flow channel from the preconditioning solution to the target solution does not exceed about one second, preferably not exceeding 500 ms, more preferably not exceeding 200 ms, and even more preferably not exceeding 100 ms. Without being bound to any particular theoretical mechanism, it is believed that during the measurement phase, a negative potential applied to the working electrode in the flow channel causes interaction of the adsorbed preconditioning species with the target solute. Generally, during the measurement phase, metal atoms deposit on the working electrode. Without being bound to any particular theoretical mechanism, it is also believed that in some cases during the measurement phase, adsorption of target solute occurs at the working electrode, possibly accompanied by desorption, incorporation and/or deactivation of preconditioning species at the working electrode.

Figure 4:
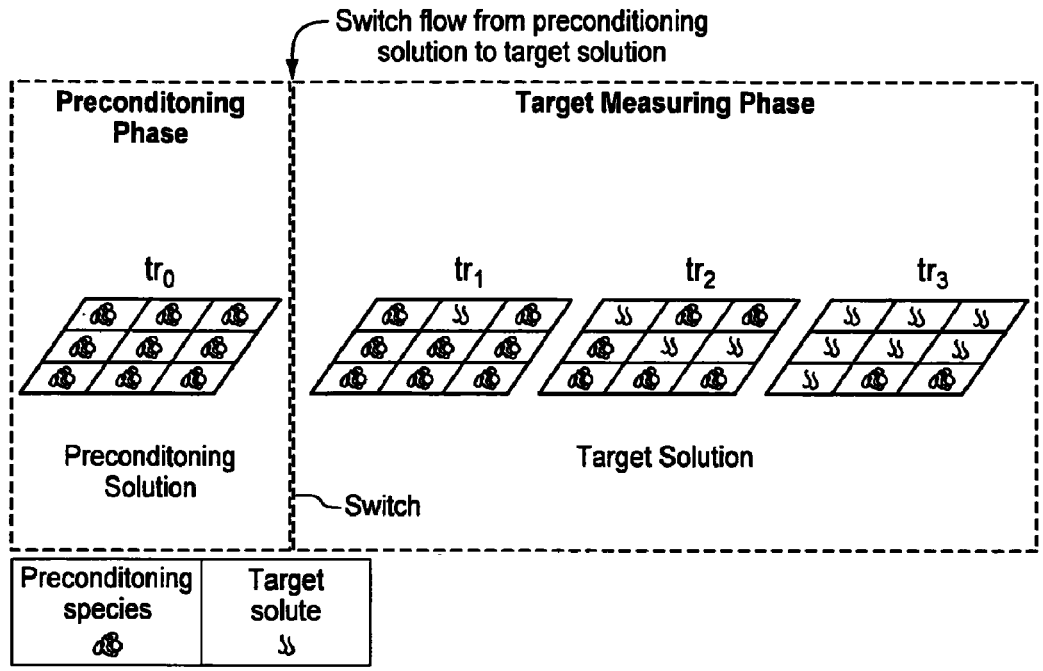
FIG. 4 depicts schematically an illustrative sequence of adsorption and desorption of preconditioning species and target solute at the surface of a working electrode in the flow channel of an electrolytic flow-through cell in accordance with the invention.

FIG. 4 depicts schematically an illustrative sequence of the interaction of preconditioning species and target solute at the surface of a working electrode in the flow channel of an electrolytic flow-through cell in accordance with the invention. At the end of the preconditioning phase, designated $tr_0$, preconditioning species absorbed to the working electrode has reached a substantially steady-state equilibrium concentration. After switching of flow through the flow channel from the preconditioning solution to the target solution, interaction of preconditioning species and target solute occurs at the working electrode. During a transient time in the target measuring phase, the concentration of target solute at the working electrode is changing with time. As depicted in FIG. 4, at the beginning of the transient time in the target measuring phase, at $tr_1$ (transient time 1), the concentration of target solute at the working electrode is relatively low. At a later transient time, $tr_2$, the concentration of target solute at the working electrode has increased, possibly accompanied by a decrease in the active concentration of preconditioning species at the electrode surface. At a still later time, $tr_3$, at or near the end of the transient time, the concentration of target solute at the working electrode has increased further, approaching a new steady-state concentration. Typically, the transient time period during which the concentrations of species at the working electrode surface change from a steady-state concentration of preconditioning species at the beginning of the transient time period to a new substantially steady-state concentration of target solute and any remaining preconditioning species has a duration of about from 20 seconds to two minutes, although the speed at which the different species interact depends on numerous factors (e.g., electric potential, additive concentrations).

In embodiments in accordance with the invention, an electrical property is measured during at least a portion of the transient time period during the target measuring phase. The changing concentrations of preconditioning species and target solute at the working electrode during the transient time result in corresponding changes in one or more measured electrical properties. In some embodiments, a constant electrical potential is applied to the working electrode so that changing transient values of current density are measured. In some embodiments, a constant current density is maintained between the working electrode and the counter electrode in the flow-through electrolytic cell and changing transient values of voltage are measured.

Example 2

An exemplary series of measurements in accordance with the invention were conducted at different known concentrations of organic accelerator additive in an electrolytic plating solution.

An electrolytic virgin make-up solution (VMS) contained in de-ionized water: 40 grams per liter (g/l) of dissolved copper metal, added as copper sulfate pentahydrate ($CuSO_4 \cdot 5H_2O$); 10 g/l $H_2SO_4$; and 50 milligram per liter (mg/l) chloride ion, added as HCl.

The preconditioning solution consisted essentially of 15 milliliter (mL) of Enthone VIAFORM® EXTREME™ suppressor per liter of VMS. The functional species of VIAFORM® EXTREME™ suppressor consists essentially of a formulation having an average molecular weight of about 2500 and a molar ratio of polypropylene glycol (PPG) to polyethylene glycol (PEG) of about 0.5. A concentration of 15 milliliters per liter (mL/L) of VIAFORM® EXTREME™ suppressor in a plating solution corresponds to a concentration of about 1500 parts per million (ppm) of the functional suppressor species in solution.

Three representative electroplating solutions in which a plating accelerator was the target solute were prepared. The first plating solution included concentrations of 5 mL/L Enthone VIAFORM® EXTREME™ accelerator, 3 mL/L Enthone VIAFORM® EXTREME™ suppressor, and 4 mL/L Enthone VIAFORM® EXTREME™ leveler in VMS, designated in this specification as a 5/3/4 solution. The functional species of VIAFORM® EXTREME™ accelerator consists essentially of bis-(3-sulfopropyl)-disulfide (SPS). A concentration of 5 mL/L of VIAFORM® EXTREME™ accelerator in a plating solution corresponds to a concentration of about 25 ppm of the functional accelerator species in the plating solution. The functional species of VIAFORM® EXTREME™ leveler consists essentially of polyvinyl pyrrolidone (PVP) having an average molecular weight in a range of about from 3,000 to 5,000. A concentration of 4 mL/L of VIAFORM® EXTREME™ leveler in a plating solution corresponds to a concentration of about 4 ppm of the functional leveler species in the plating solution. The second plating solution was a 9/3/4 solution, containing 9 mL/L Enthone VIAFORM® EXTREME™ accelerator, 3 mL/L Enthone VIAFORM® EXTREME™ suppressor, and 4 mL/L Enthone VIAFORM® EXTREME™ leveler in VMS. The third plating solution was a 13/3/4 solution, containing 13 mL/L Enthone VIAFORM® EXTREME™ accelerator, 3 mL/L Enthone VIAFORM® EXTREME™ suppressor, and 4 mL/L Enthone VIAFORM® EXTREME™ leveler in VMS.

An oxidizing cleaning solution contained 10% $H_2SO_4$, 10% $H_2O_2$, and 80% deionized water.

A measuring system in accordance with the invention included a flow-through electrolytic cell having a Ag/AgCl similar to flow-through cell 100 described above in Example 1 with reference to FIG. 2. The measuring system also included a fast-switching three-way micro-valve and two micro-annular gear pumps. The flow-through electrolytic cell together with a potentiostat, the fast-switching micro-valve and the micro-annular gear pumps were assembled in a manner described above with reference to flow-through meter 206, valve 208, and pumps 220, 222 depicted in FIG. 3. The fast-switching three-way micro-valve was a model RHEODYNE® TITAN®EX MLP777-603 valve commercially available from IDEX® Corporation, which has a switching time of approximately 150 milliseconds. The micro-annular gear pumps were model mzr-2942 gear pumps commercially available from HNP Mikrosysteme GmbH, Parchim, Germany, which are operable to initiate flow and ramp quickly (within 1 second) to required flow.

The flow-through electrolytic cell was cleaned by pumping oxidizing cleaning solution through the flow channel at a flow rate of approximately 10 mL per minute for about two minutes, followed by rinsing with deionized water at a flow rate of about 10 milliliters per minute (mL/min) for two minutes. Then, in a preconditioning phase, preconditioning solution containing the suppressor species was pumped through the flow channel at a flow rate of approximately 10 mL per minute for about two minutes. A constant potential of –0.3 V relative to the Ag/AgCl reference electrode was applied continuously to the working electrode during the preconditioning phase and the target measuring phase. The current density was measured during the preconditioning phase and during the target measuring phase. After approximately 102 seconds of measuring current density during the preconditioning phase, the valve was switched so that the flow of liquid through the flow channel of the flow-through electrolytic cell switched from the preconditioning solution to the target solution containing known concentrations of plating additives. The complete replacement of the solution to which the working electrode was exposed occurred within a switching time of about 150 ms. In the target measuring phase, the target solution was pumped through the flow channel at a flow rate of approximately 10 mL per minute. The current density was measured during the target measuring phase for at least about 20 seconds. This procedure was conducted completely for each of the three target solutions.

Figure 5:
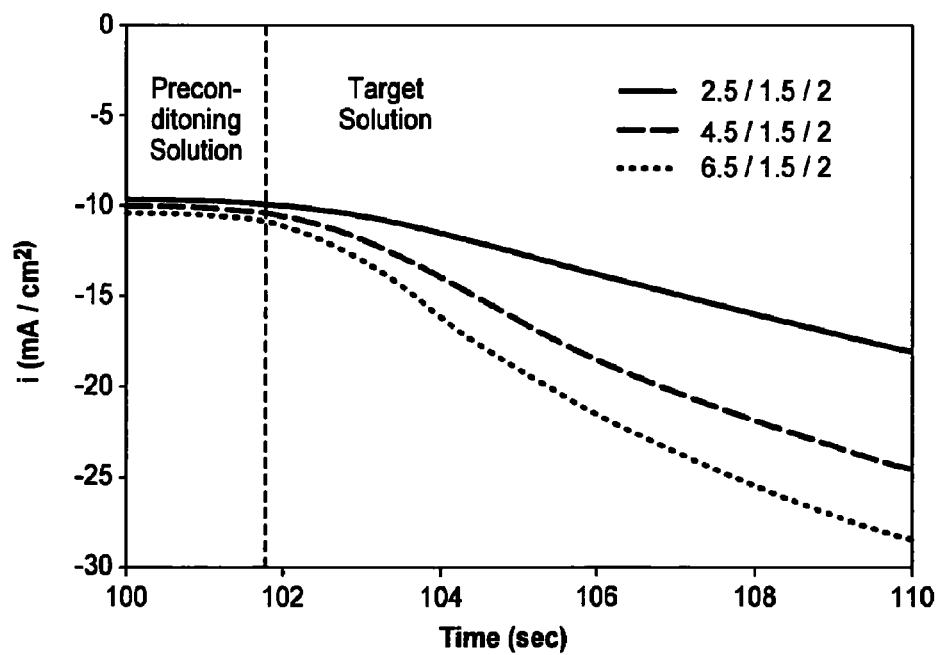
FIG. 5 contains a graph in which current density, i, in units of milliamps per centimeter squared ($mA/cm^2$) is plotted as a function of measuring time.

FIG. 5 contains a graph in which current density, i, in units of milliamps per centimeter squared ($mA/cm^2$) is plotted as a function of measuring time. As explained in more detail below, the plating solutions described above were diluted in half using VMS prior to measurement to make the actual target solutions that were measured, as indicated by the legend for the curves in the graph. As depicted in the graph of FIG. 5, at the end of the preconditioning phase before the time of 102 seconds, the current density is substantially constant, corresponding to a steady-state saturation concentration of suppressor preconditioning species at the working electrode. After switching the flow of preconditioning solution to a flow of target solution at a time about 102 seconds in each of the three exemplary measurements, the measured negative current densities substantially immediately began to increase with time, which corresponded to the unsteady-state transient concentrations of preconditioning species and target solute at the working electrode. As the concentration of preconditioning suppressor species decreased with time and the concentration of target accelerator solute increased with time during a transient time, the negative current density increased. After the time of 102 seconds, the negative current density increased at a substantially linear rate for at least about eight seconds. As explained in more detail below, during at least an initial portion of the transient time (e.g., the eight seconds from time 102 to 110 seconds), the concentration of suppressor and leveler in the target solutions did not affect the response of the accelerator in the target solution to the initially suppressed working electrode. The substantially linear response slope of each of the curves corresponding to each of the different target solutions indicate that the rate of increase of negative current density increases with increased accelerator concentration. The curves of the graph in FIG. 5 also indicate that the substantially linear transient rate of change of measured current density is usable to determine the unknown concentration of accelerator in a target solution.

The results of Example 2 show that by comparing the transient rate of change of current density in a target solution having an unknown concentration with the transient rate of change measured in one or more solutions having known concentrations of accelerator, the unknown concentration is ascertainable. For example, comparing the transient response slope (similar to the transient response slopes in the graph of FIG. 5) with transient response slopes generated using known concentrations, the unknown concentration is determined.

Figure 6:
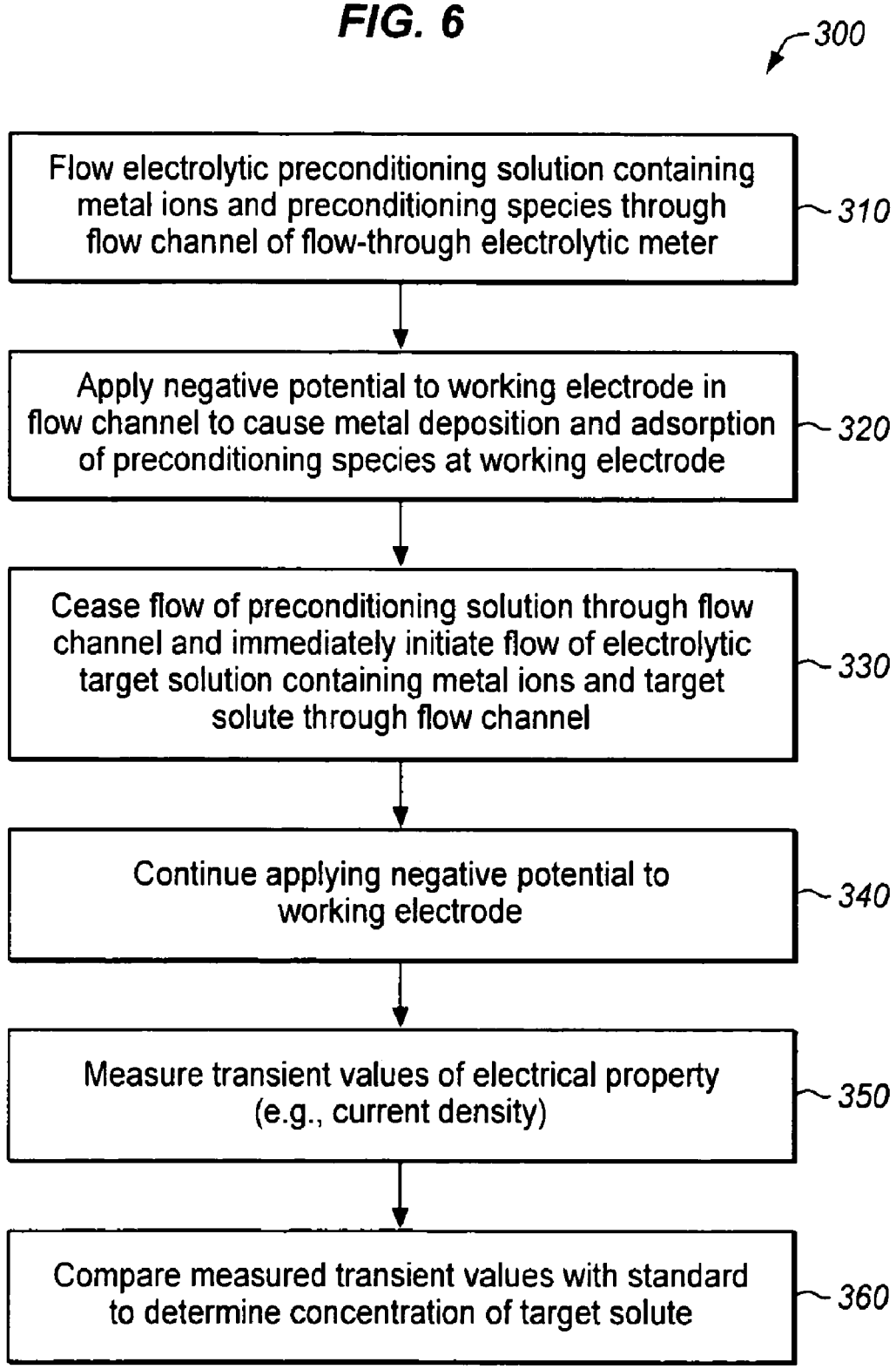
FIG. 6 contains a process flow sheet of a generalized method in accordance with the invention for measuring the concentration of a target solute in an electrolytic solution.

FIG. 6 contains a process flow sheet 300 of a generalized method in accordance with the invention for measuring the concentration of a target solute in an electrolytic solution. Process step 310 includes flowing an electrolytic preconditioning solution containing metal ions and a preconditioning species through a flow channel of a flow-through electrolytic meter. Process step 320 includes applying negative potential to the working electrode in the flow channel to cause metal deposition and adsorption of preconditioning species at the working electrode. Process step 330 includes ceasing the flow of preconditioning solution through the flow channel and immediately initiating flow of electrolytic target solution containing metal ions and target solute through the flow channel. Process step 340 includes continuing applying negative potential to the working electrode while flowing electrolytic target solution through the flow channel. Process step 350 includes measuring transient values of at least one electrical property (e.g., current density) using the flow-through electrolytic meter while the electrolytic target solution flows through the flow channel. Process step 360 includes comparing measured transient values with a standard to determine the concentration of target solute. Generally, a standard is generated for a known concentration of accelerator using techniques described in this specification; for example, techniques similar to those used in Example 2. In some embodiments, a standard for known concentration comprises a transient response curve; for example, a transient response curve generated in a manner similar to one of the curves in the graph of FIG. 5. Generally, a set of standards is developed within a range of concentrations so that the transient response generated measuring a target solution having unknown concentration can be compared with the transient responses of known, standard concentrations. A general method of developing a standard includes substantially the same steps as process flow sheet 300 not including process step 360. In this specification, transient responses measured in accordance with the invention are presented as response curves, such as in FIG. 5. It is understood that in some embodiments, transient values of an electrical property measured in accordance with the invention are recorded electronically and calculations to generate transient response standards from known concentrations and transient responses for unknown concentrations of a target solute in target solutions are performed completely electronically without actually plotting data and generating curves on graphs. For example, without actually plotting data on a graph, it is simple to calculate a substantially linear transient rate of change of current density from measured transient values of current density during a short transient time period at the beginning of a target measuring phase immediately after switching flow in a flow channel from preconditioning solution to target solution. Of course, as one of ordinary skill in the art understands, the transient response used to characterize and measure a solute concentration need not necessarily be a linear rate of change of an electrical property. For example, especially using computers, a characteristic transient response may be a characteristic nonlinear rate of change for a given concentration of solute. The characteristic transient response (e.g., a characteristic nonlinear curve or equation) may be determined using measured transient values in accordance with the invention to establish a set of standards, and then the transient response of an unknown concentration of solute may be determined and compared with the standards to ascertain the unknown concentration.

Methods in accordance with the invention are described herein mainly with reference to electrolytic copper plating solutions and the measurement of concentrations of organic additives in copper plating solutions. It is understood that in some embodiments in accordance with the invention, generalized method 300 includes one or more additional process steps. For example, in some embodiments, it is advantageous to add an electrolyte species to a liquid containing a target solute to generate a suitably electrolytic solution. In some embodiments, it is advantageous to add to a liquid solution one or more activator species that changes the chemical composition or behavior of one or more solutes in the solution to facilitate measurement of transient values of an electric property. For example, in some embodiments, a target solute precursor present in a liquid solution may not adsorb and desorb satisfactorily, but addition of an activator species generates a target solute having desirable adsorption and desorption characteristics.

When measuring the concentration of a target solute in an electrolytic solution by monitoring the transient response of an electrical property in accordance with the invention, the accuracy of the measurement depends on avoiding a substantial influence of one or more other solutes in the target solution on the transient response. For example, when measuring the concentration of accelerator additive in an electrolytic plating solution (as in Example 2 above), a condition must be established such that suppressor and leveler species present in the electrolytic plating bath do not substantially influence the transient response measured using the flow-through electrolytic meter. In methods in accordance with the invention, several means are used to avoid or to minimize the influence of other solutes on the measured transient response. Flowing preconditioning solution through the flow channel while applying a negative potential to the working electrode preconditions the working electrode by saturating it with adsorbed preconditioning species. As a result, the transient response measured in the flow-through electrolytic cell is sensitive to the concentration of target solute and relatively insensitive (at least during an initial time period) to one or more other solutes that might be present at expected concentration ranges. For example, when measuring the concentration of accelerator in an electrolytic plating bath, the working electrode is preconditioned by flowing a preconditioning solution containing suppressor species through the flow channel and applying a negative potential to the working electrode so that the working electrode becomes saturated with adsorbed suppressor species. During an initial period of the transient time in the target measuring phase, the adsorbed suppressor species causes suppressor in the target solution to be repelled. Also, leveler species present in the target solution only absorb to the surface of the working electrode (and thereby influence the measured transient values of the electrical response) when there are substantially no other additives present on the electrode or when an activated amount of accelerator has deposited onto the electrode. To reduce the interaction of the target solute with one or more other solutes, some embodiments include diluting an original bath solution to make the target solution used for measurement. For example, in Example 2 above, electroplating solutions having representative ranges of additive (accelerator, suppressor, leveler) concentrations were diluted in half. Also in Example 2, the electrochemical response of the diluted solution was analyzed during a relatively short transient time of only about eight seconds, before the leveler in the target solution interacted with the activated accelerator at the surface of the working electrode. Studies have shown that methods in accordance with the invention, such as the exemplary method of Example 2 used to measure plating accelerator concentration, are useful even with large variations in the concentration of other plating additives.

Example 3

Indirect measurements of accelerator concentration were performed in accordance with the invention at various representative concentrations of suppressor and leveler at different nominal concentrations of accelerator. A representative exemplary electroplating bath solution has a composition of 9 mL/L Enthone VIAFORM® EXTREME™ accelerator, 2 mL/L Enthone VIAFORM® EXTREME™ suppressor, and 3 mL/L Enthone VIAFORM® EXTREME™ leveler in VMS; that is, a 9/2/3 solution using the notation of this specification. Representative requirements of a measuring system in a commercial electroplating system using a 9/2/3 playing solution include the ability to monitor organic plating additives within 5% accuracy within the following concentration ranges: accelerator, 9 mL/L±2 mL/L; suppressor, 2 mL/L±1 mL/L; leveler, 3 mL/L±1 mL/L. Accordingly, measurements were made using electroplating solutions having an accelerator concentration of 5 mL/L, 9 mL/L and 13 mL/L. At each of these three accelerator concentrations, solutions were made having the following suppressor:leveler concentration combinations: 3 mL/L: 4 mL/L and 1 mL/L: 2 mL/L.

Measurements were conducted in a manner similar to that used in Example 2, with each of the solutions being diluted in half with VMS prior to measurement. Measurements were conducted at least three times for each combination of additive concentrations, with the exception of the 2.5/0.5/1 solution (i.e., 5/1/2 divided by two) for which only two measurements were performed because the two results were almost identical. FIG. 7 contains a graph in which in which the mean slope of the transient rate of change of current density per second (converted to positive values) is plotted with standard deviation bars as a function of accelerator concentration in the diluted target solutions. For example, the circle and standard deviation bars at accelerator concentration 6.5 mL/L (i.e., 13 mL/L÷2) represent six measurements: three measurements at 6.5/0.5/1 (originally 13/1/2) and three measurements at 6.5/1.5/2 (originally 13/3/4). The data of the graph in FIG. 7 indicate good measurement accuracy substantially independent of additive concentrations within the tested ranges.

Example 4

Figure 9:
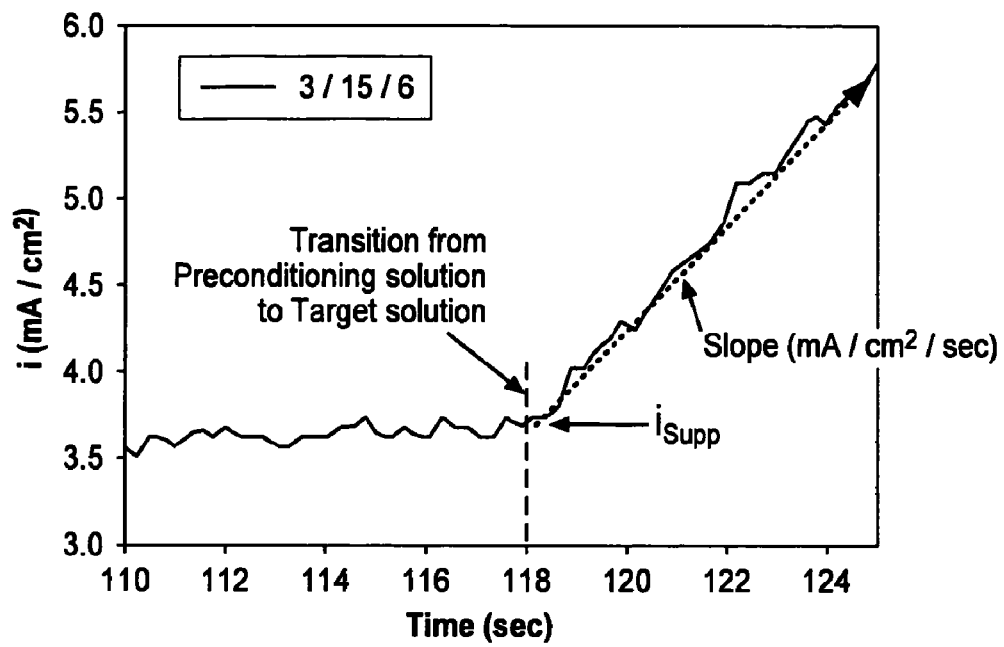
FIG. 9 contains a graph in which current density responsive to accelerator is plotted as a function of time.

Indirect measurements of accelerator concentration were conducted in a manner similar to the procedures used in Examples 2 and 3 using electroplating solutions at 12 different combinations of additive concentrations. FIG. 8 contains a graph in which current density is plotted as a function of time. The target measuring phase during which transient values of current density were measured began at about 118 seconds, indicated on the graph. The various combinations of additives are indicated in FIG. 8 using the notation described in Example 2. The data curves in the graph indicate that the slope (rate of change) of current density versus time remained substantially the same for different solutions having the same accelerator concentration but different concentrations of other additives. FIG. 9 contains a graph in which current density is plotted as a function of time from data obtained using the 3/15/6 plating solution containing 3 mL/L accelerator, 15 mL/L suppressor, and 6 mL/L leveler. In the preconditioning phase prior to the time of 118 seconds, the relatively constant current of about 3.5 mA/cm$^2$ was the result of the electrode being saturated with preconditioning suppressor molecules. After flow of liquid through the flow channel was switched to the target solution at about 118 seconds, the slope of current density versus time was substantially linear for at least about seven seconds.

Example 5

Figure 10:
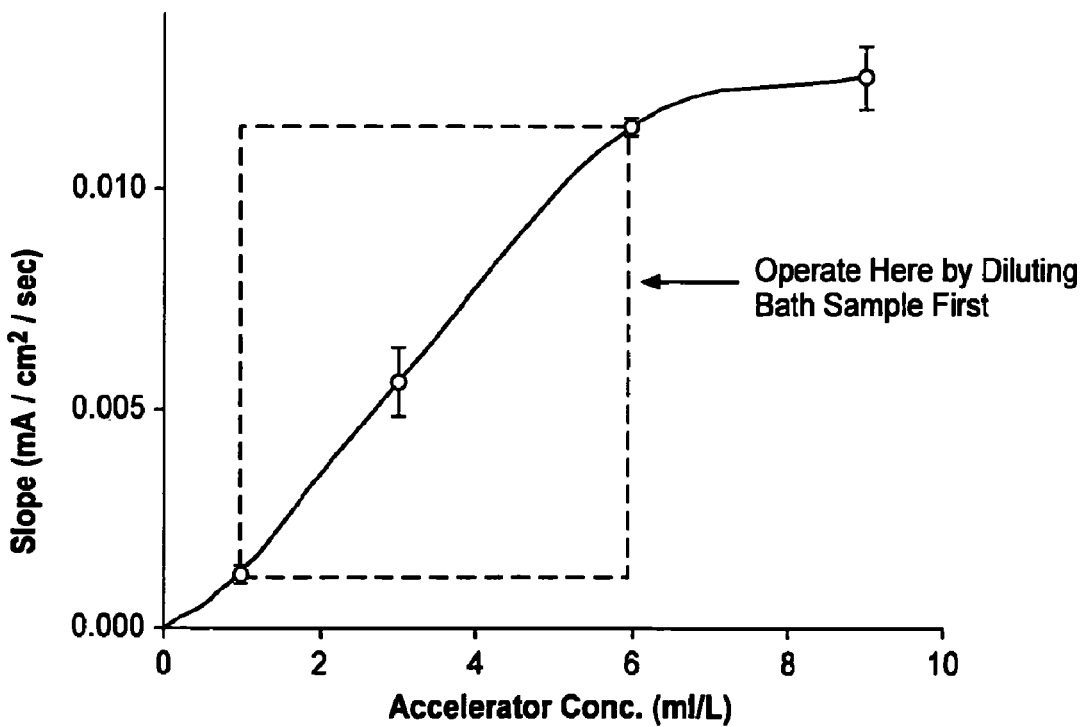
FIG. 10 contains a graph in which measured slope value in units of $mA/cm^2/sec$ is plotted as a function of accelerator concentration.

Indirect measurements of accelerator concentration were conducted in a manner similar to the procedures used in Examples 2 and 3 using electroplating solutions having accelerator concentrations of 1 mL/L, 3 mL/L, 6 mL/L, and 9 mL/L. FIG. 10 contains a graph in which measured slope value in units of mA/cm$^2$/sec is plotted as a function of accelerator concentration, where the slope values correspond to the transient rate of change of current density determined using methods in accordance with the invention, as described above in Examples 2 and 4. The data presented in FIG. 10 indicate that the transient response of measured current density varies substantially linearly with accelerator concentration up to an accelerator concentration of about 6 mL/L. This substantially linear dependence of transient response of current density on accelerator concentration is desirable because it facilitates reliably accurate monitoring of accelerator concentration. Accordingly, when methods in accordance with the invention are used to determine accelerator concentration in electroplating baths having a nominal accelerator concentration of 6 mL/L or greater, the electroplating baths solution is diluted by an appropriate amount of VMS in order to adjust the accelerator concentration in the target solution to the desired range of less than 6 mL/L.

Figure 11:
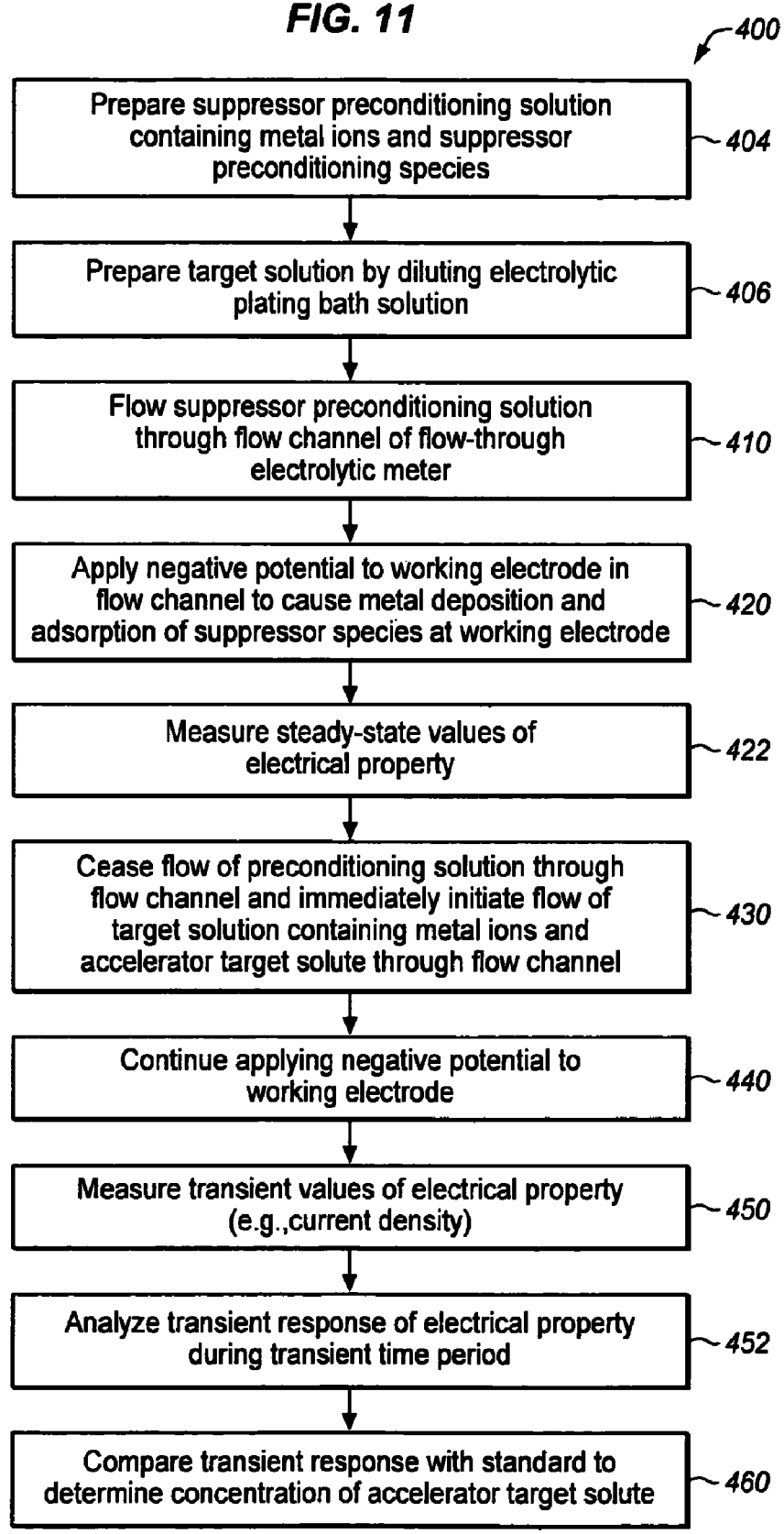
FIG. 11 contains a process flow sheet of a generalized method in accordance with the invention for measuring the concentration of accelerator additive in an electrolytic plating solution.

FIG. 11 contains a process flow sheet 400 of a generalized method in accordance with the invention for measuring the concentration of accelerator additive in an electrolytic plating solution. It is understood that some embodiments do not include all of the process steps of process flow sheet 400. For example, in some embodiments, it is not necessary to dilute the electroplating bath to make a target solution. Specific operating parameters, such as applied negative potential, compositions and concentrations of preconditioning and target solutions, and flow rates, included in the following description of process flow sheet 400 are applicable for target solute measurements comparable to those in Examples 2-5. One of ordinary skill in the art will understand that measurements in accordance with the invention involving different conditions, such as different measuring equipment and different compositions and concentrations of electroplating bath solutions, will involve different operating parameters.

Process step 404 includes preparing a suppressor preconditioning solution containing metal ions and suppressor preconditioning species. A suppressor preconditioning solution preferably has sufficiently high concentration of suppressor species so that the working electrode of the flow-through electrolytic cell becomes saturated with suppressor species during the preconditioning phase. In some embodiments, a suppressor preconditioning solution is prepared by adding a plating suppressor (e.g., a commercially available copper plating suppressor such as Enthone VIAFORM® EXTREME™ suppressor) to a virgin electroplating solution, that is, to an electroplating solution (e.g., VMS, described above) that does not include any other organic plating attitudes. The concentration of suppressor additive in a suppressor preconditioning solution is typically (though not necessarily) greater than the concentration of suppressor in electroplating solution actually used for bottom-filling. For example, the concentration of Enthone VIAFORM® EXTREME™ suppressor in electroplating bath used for bottom-filling is typically in the range of about from 1 mL/L to 5 mL/L. In contrast, in some embodiments, the concentration of Enthone VIAFORM® EXTREME™ suppressor in a suppressor preconditioning solution is 15 mL/L.

A method for measuring accelerator concentration typically (but not always) includes a process step 406, which comprises preparing a target solution by diluting an electrolytic plating bath solution with an appropriate base liquid; for example, an electrolytic solution containing no plating additives, such as VMS. As explained above with reference to FIG. 10, the concentration of accelerator in an electroplating solution commonly used for bottom-filling copper into features having high aspect ratios is sometimes higher than a preferred range of accelerator concentrations in which the transient response (e.g., the slope of current density over time) varies linearly with concentration. For this reason, electroplating solution from an electroplating bath of an actual electroplating process may be diluted appropriately to lower accelerator concentration to a desired transient-response measuring range. For example, when the electroplating bath solution has an accelerator concentration of 15 mL/L, it may be diluted with VMS by a factor of two or three to adjust the accelerator concentration to a value of 7.5 mL/L or 5 mL/L, respectively.

Process step 410 includes flowing suppressor preconditioning solution through the flow channel of a flow-through electrolytic cell. In embodiments in which the flow-through electrolytic meter includes a flow-through electrolytic cell similar to electrolytic cell 100 described in Example 1, exemplary flow rates of suppressor preconditioning solution are in a range of about from 1 milliliters per minute (mL/min) to 5 mL/min. Process step 420 includes applying negative potential to the working electrode in the flow channel to cause metal deposition and adsorption of suppressor species at the working electrode while suppressor preconditioning solution is flowing through the flow channel during the preconditioning phase. Representative durations of simultaneous process steps 410 and 420 during which negative potential is applied to the working electrode while suppressor preconditioning solution flows through the flow travel are 60 seconds to 120 seconds, although the exact duration time is usually not critical. Representative negative potential values at the working electrode are in a range of about from −0.2 to −0.5 V relative to the Ag/AgCl reference electrode. In preferred embodiments, process 400 includes process step 422 in which one or more substantially steady-state values of the electrical property (e.g., current density) are measured using the flow-through electrolytic meter before switching flow, although this steady-state measurement is not absolutely necessary.

Process step 430 includes switching the flow of liquid through the flow channel from suppressor preconditioning liquid to the target solution that contains the accelerator species. Process step 430, therefore, includes ceasing the flow of preconditioning solution through the flow channel and immediately initiating flow of target solution from the flow channel. Preferably, although not necessarily, switching the flow of liquid from the preconditioning solution to the target solution is effected in a switching time not exceeding one second, more preferably not exceeding 500 ms. Representative flow rates of target solution for the flow channel of an electrolytic cell similar to electrolytic cell 100 are in a range of about from 1 mL/min to 5 mL/min. Process step 440 includes applying negative potential during the target measuring phase, which begins when target solution begins flowing across the working electrode and continues. Representative negative potential values applied at the working electrode are in a range of about from −0.2 to −0.5 V relative to the reference electrode. Preferably, although not necessarily, the negative potential applied at the working electrode is the same during process step 420 (preconditioning phase) and process step 440 (target measuring phase). Preferably, although not necessarily, the negative potential applied to the working electrode is not interrupted during or between process steps 420 and 440.

Process step 450 includes measuring transient values of an electrical property during an initial transient time immediately after switching liquid flow in process step 430. In process 400, current density is measured at least a plurality of times, and preferably substantially continuously, during the transient time. Measurements of transient values of the current density by the flow-through electrolytic cell are performed generally at the least for an initial transient time period during which the rate of change of transient values over time is substantially linear. A representative range of an initial transient time period is about five to 15 seconds, commencing immediately upon switching liquid flow in process step 430.

Process step 452 includes calculating the transient response of the electrolytic measuring system by analyzing the plurality of transient values measured using the electrolytic cell. A representative calculation comprises calculating the rate of change of current density over time. For example, in the graphs of FIGS. 5, 8 and 9, values of current density were plotted as a function of time to determine a substantially linear rate of change (linear slope) for each of a plurality of accelerator concentrations. Of course, as one of ordinary skill in the art will understand, the transient response used to characterize and measure accelerator concentration need not necessarily be a linear rate of change of an electrical property. For example, especially using computers, a characteristic transient response may be a characteristic nonlinear rate of change for a given concentration of accelerator.

Process step 460 comprises comparing the transient response calculated in process step 452 with one or more standard responses generated using known concentrations of target solute to determine the concentration of target solute. One of ordinary skill in the art will understand that standard responses for comparison in process step 460 are also generated using the process steps of process flow sheet 400.

In some embodiments, the electrolytic preconditioning solution comprises functional suppressor species consisting essentially of polyethylene glycol (PEG) polymers and polypropylene glycol (PPG) polymers (or block copolymers of the two) having an average molecular weight in a range of about from 1500 to 3500, at a molar ratio of PPG to PEG, PPG:PPE, in a range of about from 0.2 to 0.8. In some embodiments, the organic plating accelerator comprises a functional species consisting essentially of bis-(3-sulfopropyl)-disulfide (SPS). In some embodiments, the electrolytic preconditioning solution has a concentration of said functional suppressor species of PPG and PEG in a range of about from 50 ppm to 1500 ppm. In some embodiments, initiating flow of electrolytic target solution in step 430 comprises flowing a target solution comprising bis-(3-sulfopropyl)-disulfide (SPS) at a concentration in a range of about from (1 ppm to 100 ppm)/2.

Example 6

Indirect measurements of suppressor concentration in accordance with the invention were conducted using procedures of generalized process flow sheet 300 and a flow-through electrolytic cell as described above in Example 1 connected to a conventional potentiostat. A measuring system in accordance with the invention included a flow-through electrolytic cell having a Ag/AgCl reference electrode in a system as described in detail in Example 3.

An oxidizing cleaning solution contained 10% $H_2SO_4$, 10% $H_2O_2$, and 80% deionized water.

An electrolytic virgin make-up solution (VMS) contained: 40 grams per liter (g/l) of dissolved copper metal, added as copper sulfate pentahydrate ($CuSO_4 \cdot 5H_2O$); 10 g/l $H_2SO_4$; and 50 milligram per liter (mg/l) chloride ion, added as HCl.

The preconditioning solution was VMS. Eight original solutions containing plating suppressor were prepared, then diluted with VMS by a factor of 32 to make eight target solutions. Four original solutions contained only suppressor additive at representative concentrations in VMS; namely, 0.5 mL/L, 1.0 mL/L, 1.5 mL/L and 2.0 mL/L Enthone VIAFORM® EXTREME™ suppressor in VMS, designated 0/0.5/0, 0/1/0, 0/1.5/0, and 0/2/0 using the notation presented earlier. Four other original solutions contained relatively high concentrations of Enthone VIAFORM® EXTREME™ accelerator and Enthone VIAFORM® EXTREME™ leveler additives. The four other solutions were designated: 12/0.5/6; 12/1.0/6; 12/1.5/6; and 12/2/6. For example, the solution designated 12/1.5/6 contained 12 mL/L Enthone VIAFORM® EXTREME™ accelerator, 1.5 mL/L Enthone VIAFORM® EXTREME™ suppressor, and 6 mL/L Enthone VIAFORM® EXTREME™ leveler in VMS. The original solutions were diluted to reduce the influence of accelerator and leveler in the target solution.

Before each measurement procedure, the flow-through electrolytic cell was cleaned by pumping oxidizing cleaning solution through the flow channel at a flow rate of approximately 10 mL/min for about two minutes, then rinsing with deionized water at a flow rate of about 10 mL/min for about two minutes.

In each preconditioning phase, VMS preconditioning solution was flowed at a flow rate of 5 mL/min through the flow channel for approximately 36 seconds and a negative potential of −0.3 V relative to the Ag/AgCl reference electrode was applied to the working electrode. As a result, the preconditioned working electrode was plated with copper having a CuCl film, which attracted suppressor during the subsequent target measurement phase. The substantially steady-state current density was measured during the preconditioning phase to determine a base current density, $i_{VMS}$.

During each of the eight suppressor concentration measurements, the target measurement phase was initiated when liquid flow through the flow channel was switched from the preconditioning solution to the target solution. The complete replacement of the solution to which the working electrode was exposed occurred within a switching time of about 150 ms. Target solution flowed through the flow channel at a flow rate of 5 mL/min and the negative potential of −0.3 V continued to be applied to the working electrode for at least about 30 seconds after initiation of the target measuring phase. Transient values of current density were measured continuously for at least about 30 seconds during the target measuring phase, during which current density, i, changed with time.

Figure 12:
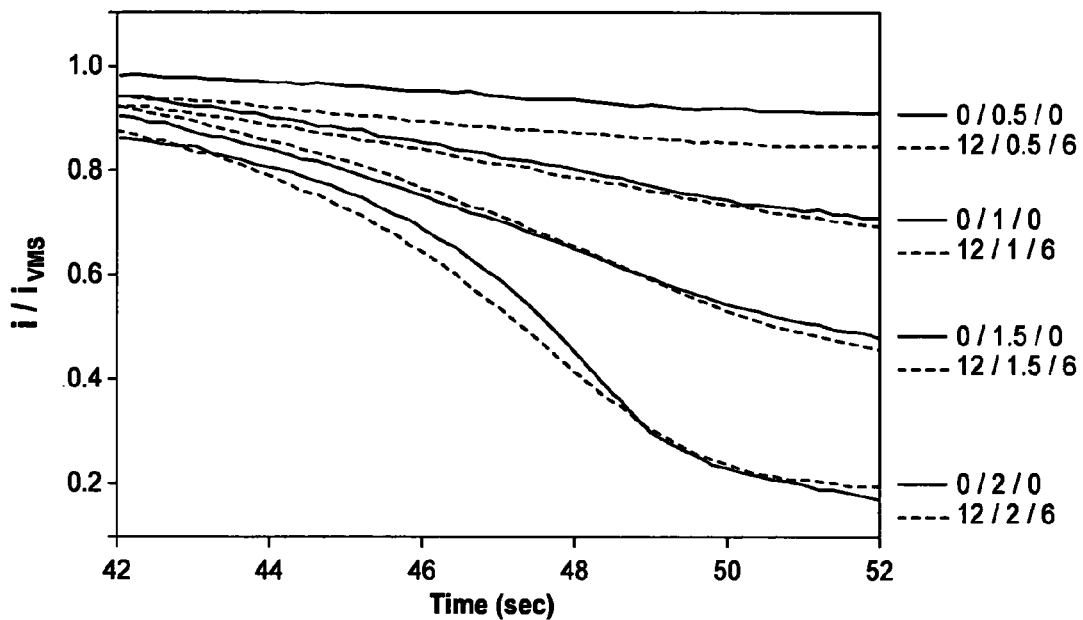
FIG. 12 contains a graph in which normalized current density, $i/i_{VMS}$, responsive to suppressor concentration is plotted as a function of measuring time.

FIG. 12 contains a graph in which normalized current density, $i/i_{VMS}$, is plotted as a function of measuring time. The curves are labeled using the concentration designations for the original solutions. The original plating solutions described above were diluted by a factor of 4 using VMS prior to measurement to make the actual target solutions. The transient response curves in FIG. 12 show a significant response (i.e., current density as a function of time) despite the dilution. The response curves also show a strong dependence of the response on the concentration of suppressor in the target solution. The response curves further show that the response at a given concentration of suppressor in the target solution is substantially independent of the concentrations of accelerator and leveler in the target solutions.

Figure 13:
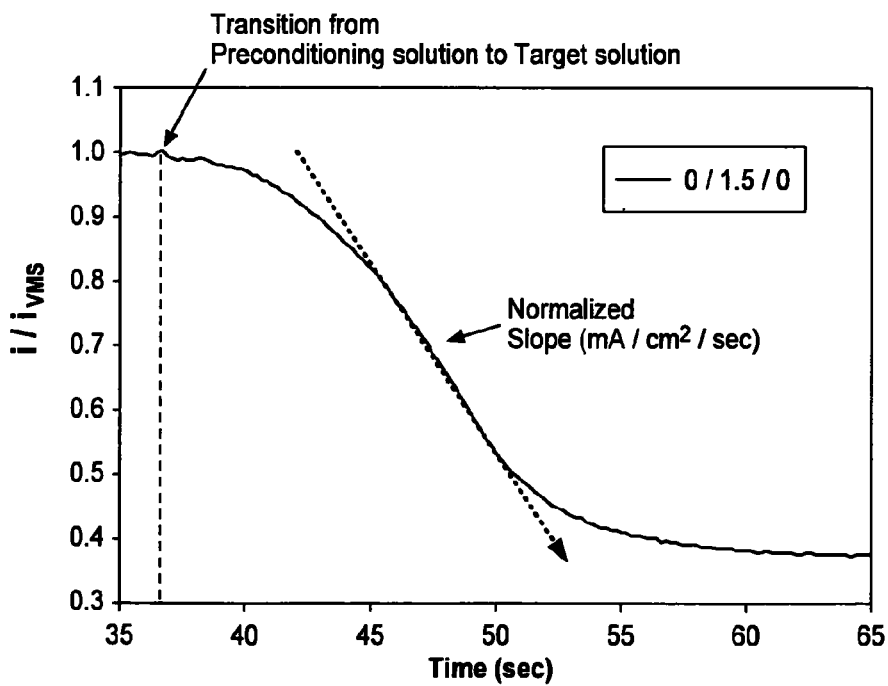
FIG. 13 contains a graph in which normalized current density responsive to suppressor concentration is plotted as a function of time.

FIG. 13 contains a graph in which normalized current density in the target 0/1.5/0 solution is plotted as a function of time. As mentioned above, the original 0/1.5/0 solution was diluted by a factor of 4 to make the target solution. The response curve and the superimposed slope lined in the time range of about from 45 to 50 seconds in the graph of FIG. 13 shows that current density changes substantially linearly with time. Referring back to the graph in FIG. 12, one can see that the response curves of solutions having different suppressor concentrations also have substantially different transient responses in the time range of about 45 to 50 seconds. The differing transient responses represented by the response curves in FIG. 12, which depend from suppressor concentration but which are relatively independent of accelerator and leveler concentrations, are useful for indirectly measuring an unknown concentration of suppressor in a target solution.

Figure 14:
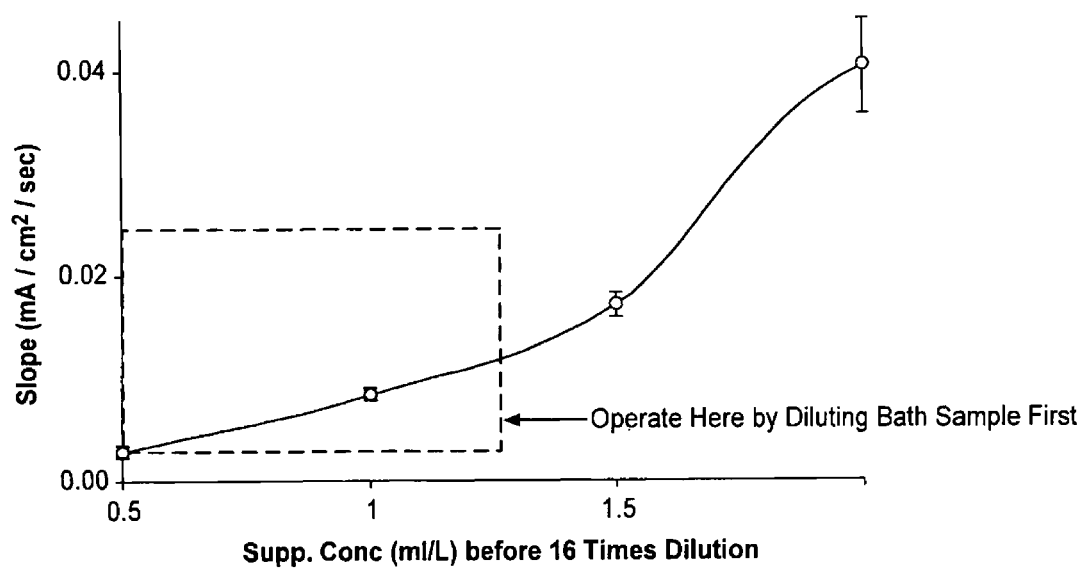
FIG. 14 contains a graph in which the average value of the linear slope of response curves at each of four suppressor concentrations was plotted as a function of original suppressor concentration (i.e., before dilution)

To examine and to demonstrate desirable ranges of accelerator and leveler in a target solution being monitored for suppressor concentration in accordance with the invention, the original eight solutions prepared above were diluted by a factor of 16 to make eight new target solutions, which were then processed using the method of this Example 6. In the graph of FIG. 14, the average value at each of the four concentrations of the linear slope of the response curves (similar to response curves in FIG. 12) was plotted as a function of original suppressor concentration (even though the actual target solution was diluted by a factor of 16). The error bars indicate the standard deviation of the two slope values at each suppressor concentration, and indicate the influence of accelerator and leveler on measurements. The data plotted in the graph of FIG. 14 indicate that the influence of accelerator and leveler, within the broad ranges of these additives used in the original solutions, was substantially insignificant when the suppressor concentration was adjusted to about (1.25/16) mL/L or less.

Figure 15:
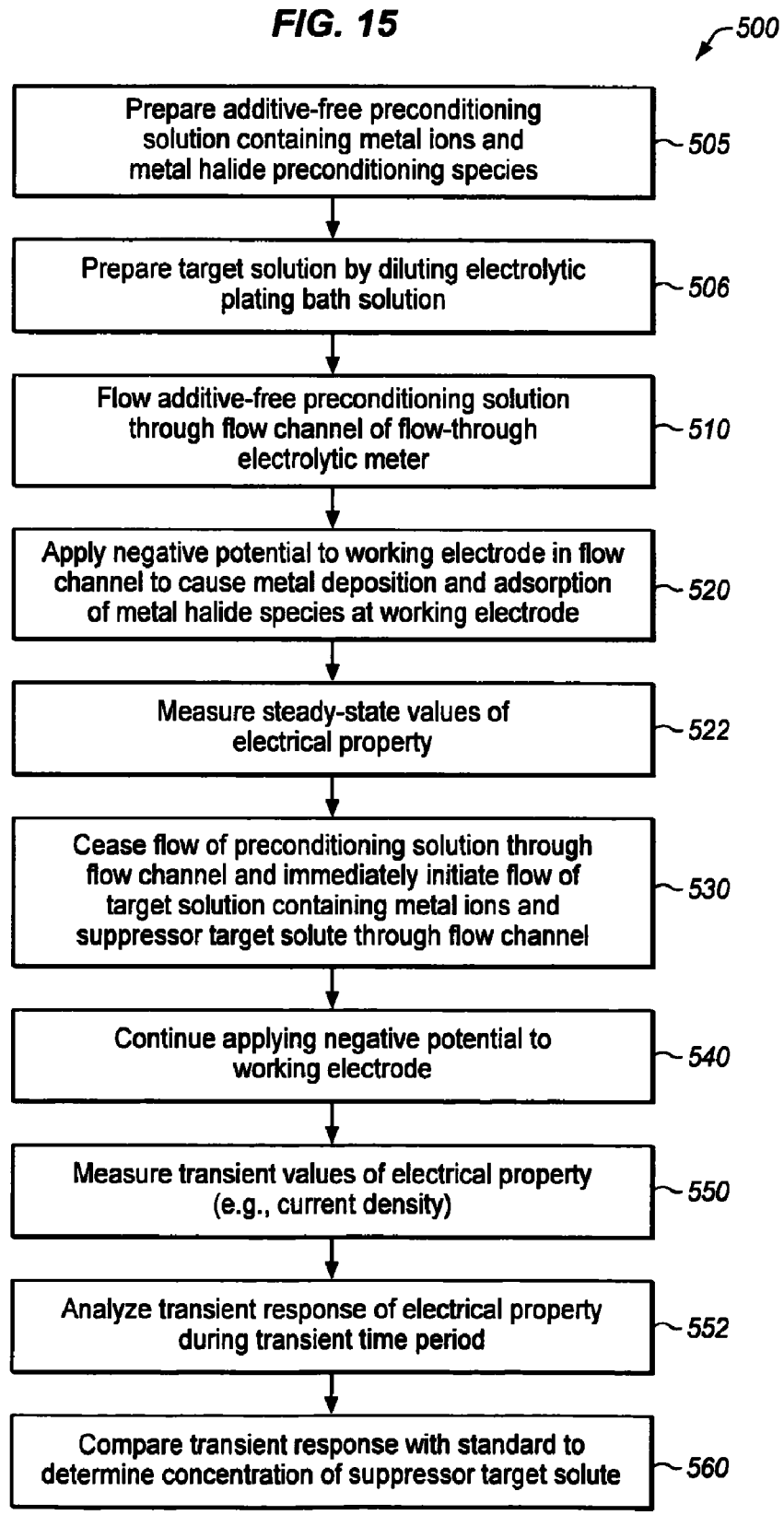
FIG. 15 contains a process flow sheet of a generalized method in accordance with the invention for measuring the concentration of suppressor additive in an electrolytic copper plating solution.

FIG. 15 contains a process flow sheet 500 of a generalized method in accordance with the invention for measuring the concentration of suppressor additive in an electrolytic copper plating solution. It is understood that some embodiments do not include all of the process steps of process flow sheet 500. For example, in some embodiments, it is not necessary to dilute the electroplating bath to make a target solution. Specific operating parameters, such as applied negative potential, compositions and concentrations of preconditioning and target solutions, and flow rates, included in the following description of process flow sheet 500 are applicable for target solute measurements comparable to those in Examples 6-8. One of ordinary skill in the art will understand that measurements in accordance with the invention involving different conditions, such as different measuring equipment and different compositions and concentrations of electroplating bath solutions, will involve different operating parameters.

Process step 505 includes preparing a substantially additive-free preconditioning solution containing metal ions and preconditioning species. In some embodiments involving measuring suppressor concentration in a copper electroplating solution, a representative additive-free and preconditioning solution is VMS, described above, which contains copper ions and chloride ions. Generally, a preconditioning solution preferably has sufficiently high concentration of metal and halide species so that the working electrode of the flow-through electrolytic cell becomes saturated with a metal halide (e.g., CuCl) film during the preconditioning phase.

A method for measuring suppressor concentration typically (but not always) includes a process step 506, which comprises preparing a target solution by diluting an electrolytic plating bath solution with an appropriate base liquid; for example, an electrolytic solution containing no plating additives, such as VMS. The concentration of suppressor in an electroplating solution commonly used for bottom-filling copper into features having high aspect ratios is sometimes higher than a preferred range of suppressor concentrations in which the transient response (e.g., the slope of current density over time) varies with concentration substantially independent of the concentration of other additives, such as accelerator and leveler. For this reason, electroplating solution from an electroplating bath of an actual electroplating process may be diluted appropriately to lower suppressor concentration to a desired transient-response measuring range. For example, when the electroplating bath solution has a suppressor concentration of 2.0 mL/L, it may be diluted with VMS by a factor of 32 to adjust the concentrations of suppressor, accelerator and leveler.

In some exemplary embodiments in accordance with the invention the preconditioning species comprises chloride ion (Cl_), and the target solute comprises functional suppressor species consisting essentially of polyethylene glycol (PEG) polymers and polypropylene glycol (PPG) polymers (or block copolymers of the two) having an average molecular weight in a range of about from 1500 to 3500, at a molar ratio of PPG to PEG, PPG:PPE, in a range of about from 0.2 to 0.8. In some embodiments, the electrolytic preconditioning solution has a chloride ion concentration in a range of about from (10 ppm to 500 ppm), and the target solution has a concentration of functional suppressor species of PPG and PEG in a range of about from (50 ppm to 600 ppm)/32.

Process step 510 includes flowing additive-free preconditioning solution (e.g., VMS) through the flow channel of a flow-through electrolytic cell. In embodiments in which the flow-through electrolytic meter includes a flow-through electrolytic cell similar to electrolytic cell 100 described in Example 1, exemplary flow rates of VMS preconditioning solution are in a range of about from 1 mL/min to 5 mL/min. Process step 520 includes applying negative potential to the working electrode in the flow channel to cause metal deposition and adsorption of CuCl preconditioning species at the working electrode while additive-free preconditioning solution is flowing through the flow channel during the preconditioning phase. Representative durations of simultaneous process steps 510 and 520 during which negative potential is applied to the working electrode while VMS preconditioning solution flows through the flow channel are 30 seconds to 100 seconds, although the exact duration time is usually not critical. Representative negative potential values at the working electrode are in a range of about from −0.2 to −0.5 V relative to the Ag/AgCl reference electrode. In preferred embodiments, process 500 includes process step 522 in which one or more substantially steady-state values of the electrical property (e.g., current density) are measured using the flow-through electrolytic meter before switching flow, although this steady-state measurement is not absolutely necessary.

Process step 530 includes switching the flow of liquid through the flow channel from additive-free preconditioning liquid to the target solution that contains the suppressor species. Process step 530, therefore, includes ceasing the flow of preconditioning solution through the flow channel and immediately initiating flow of target solution from the flow channel. Preferably, although not necessarily, switching the flow of liquid from the preconditioning solution to the target solution is effected in a switching time not exceeding one second, more preferably not exceeding 500 ms. Representative flow rates of target solution for the flow channel of an electrolytic cell similar to electrolytic cell 100 are in a range of about from 1 mL/min to 5 mL/min. Process step 540 includes applying negative potential during the target measuring phase, which begins when target solution begins flowing across the working electrode and continues. Representative negative potential values applied at the working electrode are in a range of about from −0.2 to −0.5 V relative to the reference electrode. Preferably, although not necessarily, the negative potential applied at the working electrode is the same during process step 520 (preconditioning phase) and process step 540 (target measuring phase). Preferably, although not necessarily, the negative potential applied to the working electrode is not interrupted during or between process steps 520 and 540.

Process step 550 includes measuring transient values of an electrical property, typically current density, during an initial transient time immediately after switching liquid flow in process step 530. In process 500, current density is measured at least a plurality of times, and preferably substantially continuously, during the transient time. Measurements of transient values of the current density by the flow-through electrolytic cell are performed generally at least for an initial transient time period during which the rate of change of transient values over time is substantially linear. A representative range of an initial transient time period is about five to 15 seconds, commencing immediately upon switching liquid flow in process step 530.

Process step 552 includes calculating the transient response of the electrolytic measuring system by analyzing the plurality of transient values measured using the electrolytic cell. A representative calculation comprises calculating the rate of change of current density over time. For example, in the graphs of FIG. 12, normalized values of current density were plotted as a function of time to determine a characteristic response curve for each of a plurality of suppressor concentrations. Of course, as one of ordinary skill in the art will understand, the transient response used to characterize and measure suppressor concentration need not be fit to any particular type of equation, such as a linear regression. For example, especially using computers, a characteristic transient response may be a characteristic nonlinear rate of change for a given concentration of suppressor. Additionally or alternatively in some embodiments, transient values of current density or other electrical property measured at given times during the target measuring phase are used to measure concentration indirectly.

Process step 560 comprises comparing the transient response calculated in process step 552 with one or more standard responses generated using known concentrations of target solute to determine the concentration of target solute. One of ordinary skill in the art will understand that standard responses for comparison in process step 560 are also generated using the process steps of process flow sheet 500. For example, response curves similar to those in FIG. 12 are useful as standards in process step 560 to compare with the transient response of an unknown concentration of suppressor in a target solution.

Example 7

Indirect measurements of suppressor concentration in accordance with the invention were conducted using procedures of generalized process flow sheet 500 and a flow-through electrolytic cell as described above in Example 1 connected to a conventional potentiostat. A measuring system in accordance with the invention included a flow-through electrolytic cell having a Ag/AgCl reference electrode in a system as described in detail in Example 3.

An oxidizing cleaning solution contained 10% $H_2SO_4$, 10% $H_2O_2$, and 80% deionized water.

An electrolytic virgin make-up solution (VMS) contained: 40 grams per liter (g/l) of dissolved copper metal, added as copper sulfate pentahydrate ($CuSO_4.5H_2O$); 10 g/l $H_2SO_4$; and 50 milligram per liter (mg/l) chloride ion, added as HCl.

The preconditioning solution was VMS. Three original solutions containing plating suppressor were prepared, then diluted with VMS by a factor of 32 to make three target solutions. The three original solutions contained relatively high concentrations of Enthone VIAFORM® EXTREME™ accelerator and Enthone VIAFORM® EXTREME™ leveler additives, and were designated: 13/1/5; 13/2/5; and 13/3/5 using the nomenclature described above. For example, the solution designated 13/2/5 contained 13 mL/L Enthone VIAFORM® EXTREME™ accelerator, 2.0 mL/L Enthone VIAFORM® EXTREME™ suppressor, and 5 mL/L Enthone VIAFORM® EXTREME™ leveler in VMS. The original solutions were diluted to reduce the influence of accelerator and leveler in the target solution.

Before each measurement procedure, the flow-through electrolytic cell was cleaned by pumping oxidizing cleaning solution through the flow channel at a flow rate of approximately 10 mL/min for about two minutes, then rinsed with deionized water at a flow rate of 10 mL/min for two minutes.

In each preconditioning phase, VMS preconditioning solution was flowed at a flow rate of 5 mL/min through the flow channel for approximately 80 seconds and a negative potential of −0.2 V relative to the Ag/AgCl reference electrode was applied to the working electrode. As a result, the preconditioned working electrode was plated with copper having a CuCl film, which attracted suppressor during the subsequent target measurement phase. The substantially steady-state current density was measured during the preconditioning phase to determine a base current density, $i_{VMS}$.

During each of the three suppressor concentration measurements, the target measurement phase was initiated when liquid flow through the flow channel was switched from the preconditioning solution to the target solution. The complete replacement of the solution to which the working electrode was exposed occurred within a switching time of about 150 ms. Target solution flowed through the flow channel at a flow rate of 5 mL/min and the negative potential of −0.2 V continued to be applied to the working electrode for at least about 40 seconds after initiation of the target measuring phase. Transient values of current density were measured continuously for at least about 40 seconds during the target measuring phase, during which current density, i, changed with time.

Figure 16:
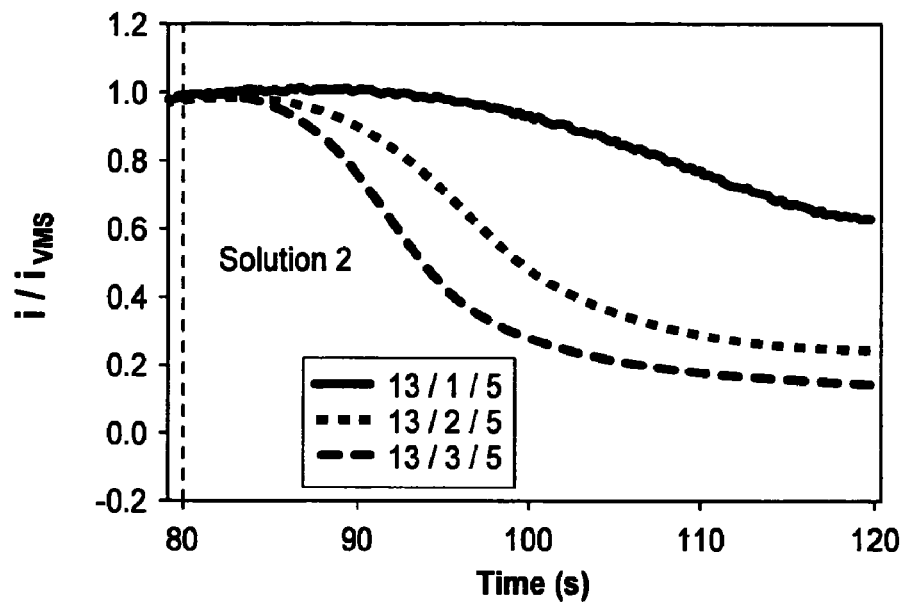
FIG. 16 contains a graph in which normalized current density, $i/i_{VMS}$, responsive to suppressor concentration is plotted as a function of measuring time.

FIG. 16 contains a graph in which normalized current density, $i/i_{VMS}$, is plotted as a function of measuring time. The curves are labeled using the concentration designations for the original solutions. The original plating solutions described above were diluted by a factor of 32 using VMS prior to measurement to make the actual target solutions. The transient response curves in FIG. 16 show a significant response (i.e., current density as a function of time) despite the dilution. The response curves also show a strong dependence of the response on the concentration of suppressor in the target solution.

Example 8

To examine and to demonstrate desirable ranges of accelerator and leveler in a target solution being monitored for suppressor concentration in accordance with the invention, three original plating solutions similar to those in Example 7 were prepared except with lower concentrations of accelerator and leveler. The three new original solutions contained relatively high concentrations of Enthone VIAFORM® EXTREME™ accelerator and Enthone VIAFORM® EXTREME™ leveler additives, and were designated: 5/1/1; 5/2/1; and 5/3/1 using the nomenclature described above. For example, the solution designated 5/2/1 contained 5 mL/L Enthone VIAFORM® EXTREME™ accelerator, 2.0 mL/L Enthone VIAFORM® EXTREME™ suppressor, and 1 mL/L Enthone VIAFORM® EXTREME™ leveler in VMS. The original solutions were diluted by a factor of 32 as in Example 7 to reduce the influence of accelerator and leveler in the target solution.

The target solutions were processed and analyzed as described above in Example 7.

Figure 17:
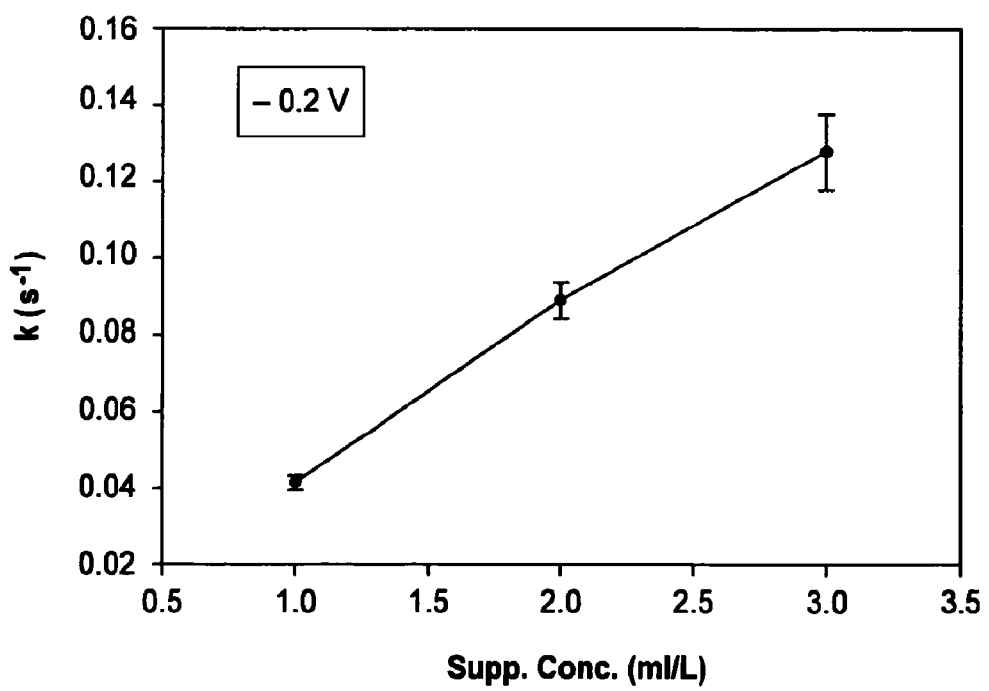
FIG. 17 contains a graph in which exponential rate constants corresponding to each of three suppressor concentrations was plotted as a function of original suppressor concentration (although the actual target solutions were diluted by a factor of 32)

Measured transient responses were fit to an exponential to calculate exponential rate constants. FIG. 17 contains a graph in which exponential rate constants corresponding to each of the three suppressor concentrations were plotted as a function of original suppressor concentration (even though the actual target solutions were diluted by a factor of 32). The error bars indicate the standard deviation of the two values of rate constant at each suppressor concentration, and indicate the influence of accelerator and leveler on measurement accuracy. The data plotted in the graph of FIG. 17 indicate that the influence of accelerator and leveler, within the broad ranges of these additives used in the original solutions, is substantially insignificant when the suppressor concentration is adjusted to about (2.0/32) mL/L or less, preferably to about (1.0/32) mL/L or less.

Example 9

Indirect measurements of leveler concentration in accordance with the invention were conducted using procedures of generalized process flow sheet 300 and a flow-through electrolytic cell as described above in Example 1 connected to a conventional potentiostat. A measuring system in accordance with the invention included a flow-through electrolytic cell having a Ag/AgCl reference electrode in a system as described in detail in Example 3.

An oxidizing cleaning solution contained 10% $H_2SO_4$, 10% $H_2O_2$, and 80% deionized water.

An electrolytic virgin make-up solution (VMS) contained: 40 grams per liter (g/l) of dissolved copper metal, added as copper sulfate pentahydrate ($CuSO_4.5H_2O$); 10 g/l $H_2SO_4$; and 50 milligram per liter (mg/l) chloride ion, added as HCl.

The preconditioning solution consisted essentially of 27 mL/L Enthone VIAFORM® EXTREME™ accelerator and 2 mL/L Enthone VIAFORM® EXTREME™ suppressor VMS. Six original solutions containing plating leveler were prepared, then diluted with VMS by a factor of 4 to make six target solutions. The six original solutions contained leveler additive at one of three representative concentrations in VMS; namely, 2 mL/L, 3 mL/L, and 4 mL/L Enthone VIAFORM® EXTREME™ leveler in VMS. Each of the original solutions also contained either relatively high or relatively low concentrations of Enthone VIAFORM® EXTREME™ accelerator and Enthone VIAFORM® EXTREME™ suppressor additives. Using the notation presented earlier, the six original solutions had additive concentrations with the following designations: 15/3/2, 151313, 1513/4, 5/1/2, 5/1/3, 5/1/4. For example, the solution designated 15/3/4 contained 15 mL/L Enthone VIAFORM® EXTREME™ accelerator, 3 mL/L Enthone VIAFORM® EXTREME™ suppressor, and 4 mL/L Enthone VIAFORM® EXTREME™ leveler in VMS. The original solutions were diluted with VMS by a factor of four to reduce the influence of accelerator and suppressor in the target solution.

Before each measurement procedure, the flow-through electrolytic cell was cleaned by pumping oxidizing cleaning solution through the flow channel at a flow rate of approximately 10 mL per minute for about two minutes, then rinsed with deionzied water at a flow rate of 10 mL/min for two minutes.

In each preconditioning phase, the accelerator/suppressor preconditioning solution was flowed at a flow rate of 5 mL/min through the flow channel for approximately 100 seconds and a negative potential of −0.18 V relative to the Ag/AgCl reference electrode was applied to the working electrode. As a result, the preconditioned working electrode was plated with copper and had an accelerated surface; that is, the working electrode was substantially saturated with accelerator species in the presence of a small amount of suppressor. The substantially steady-state current density achieved during the preconditioning phase was measured at the end of the preconditioning phase to determine a base current density, $i_{acc}$.

During each of the six leveler concentration measurements, the target measurement phase was initiated when liquid flow through the flow channel was switched from the preconditioning solution to the target solution. The complete replacement of the solution to which the working electrode was exposed occurred within a switching time of about 150 ms. Target solution flowed through the flow channel at a flow rate of 5 mL/min and the negative potential of −0.18 V continued to be applied to the working electrode for at least about 20 seconds after initiation of the target measuring phase. Transient values of current density were measured continuously for at least about 20 seconds during the target measuring phase, during which current density, i, changed with time.

Figure 18:
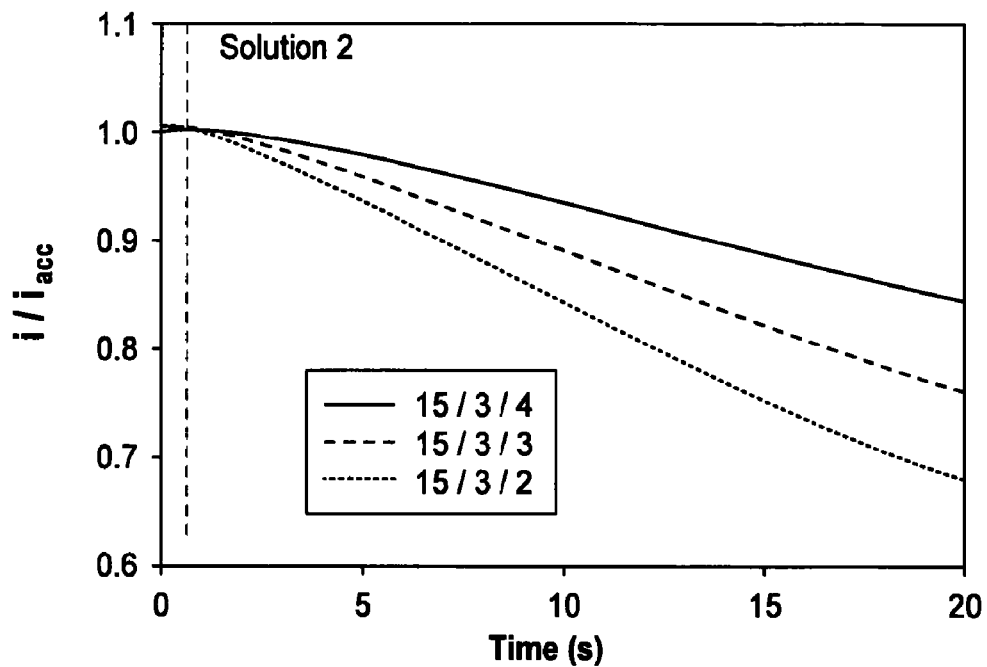
FIG. 18 contains a graph in which normalized current density, $i/i_{VMS}$, responsive to leveler concentration is plotted as a function of measuring time.

FIG. 18 contains a graph in which normalized current density, $i/i_{acc}$, is plotted as a function of measuring time. The three transient response curves are labeled using the concentration designations for the original solutions. The original plating solutions described above were diluted by a factor of 4 using VMS prior to measurement to make the actual target solutions. The transient response curves in FIG. 18 show a significant response (i.e., current density as a function of time) despite the dilution of the target leveler solute. The response curves also show a strong dependence of the response on the concentration of leveler in the target solution.

Figure 19:
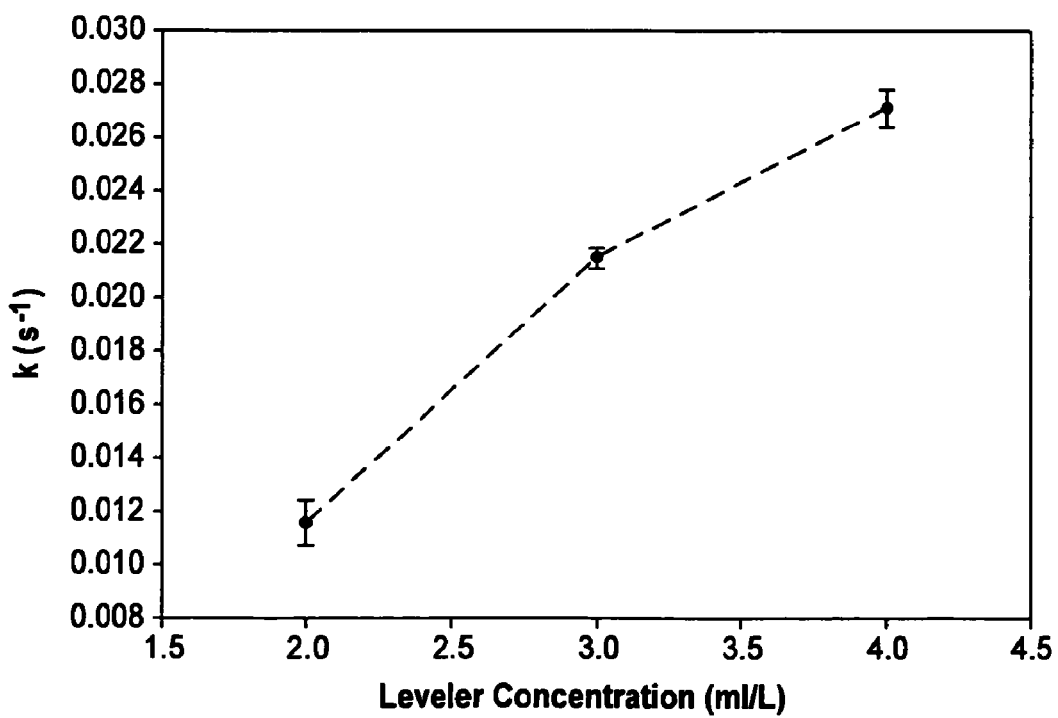
FIG. 19 contains a graph in which average exponential rate constant was plotted as a function of leveler concentration.

To examine and to demonstrate desirable ranges of accelerator and suppressor in a target solution being monitored for leveler concentration in accordance with the invention, the transient response data measured for each of the six target solutions were fitted to an exponential and the corresponding rate constant for each set of six transient response data was calculated. In the graph of FIG. 19, the average of two rate constants was plotted as a function of leveler concentration. For example, the average of the rate constant calculated from measured transient values associated with the 5/1/2 and the 15/3/2 solutions was plotted. The standard-deviation error bars in the graph of FIG. 19 indicate that the transient response during the target measuring phase was substantially independent of the concentrations of accelerator and suppressor, particularly when the target solution had a leveler concentration of about 3 mL/L divided by four.

Figure 20:
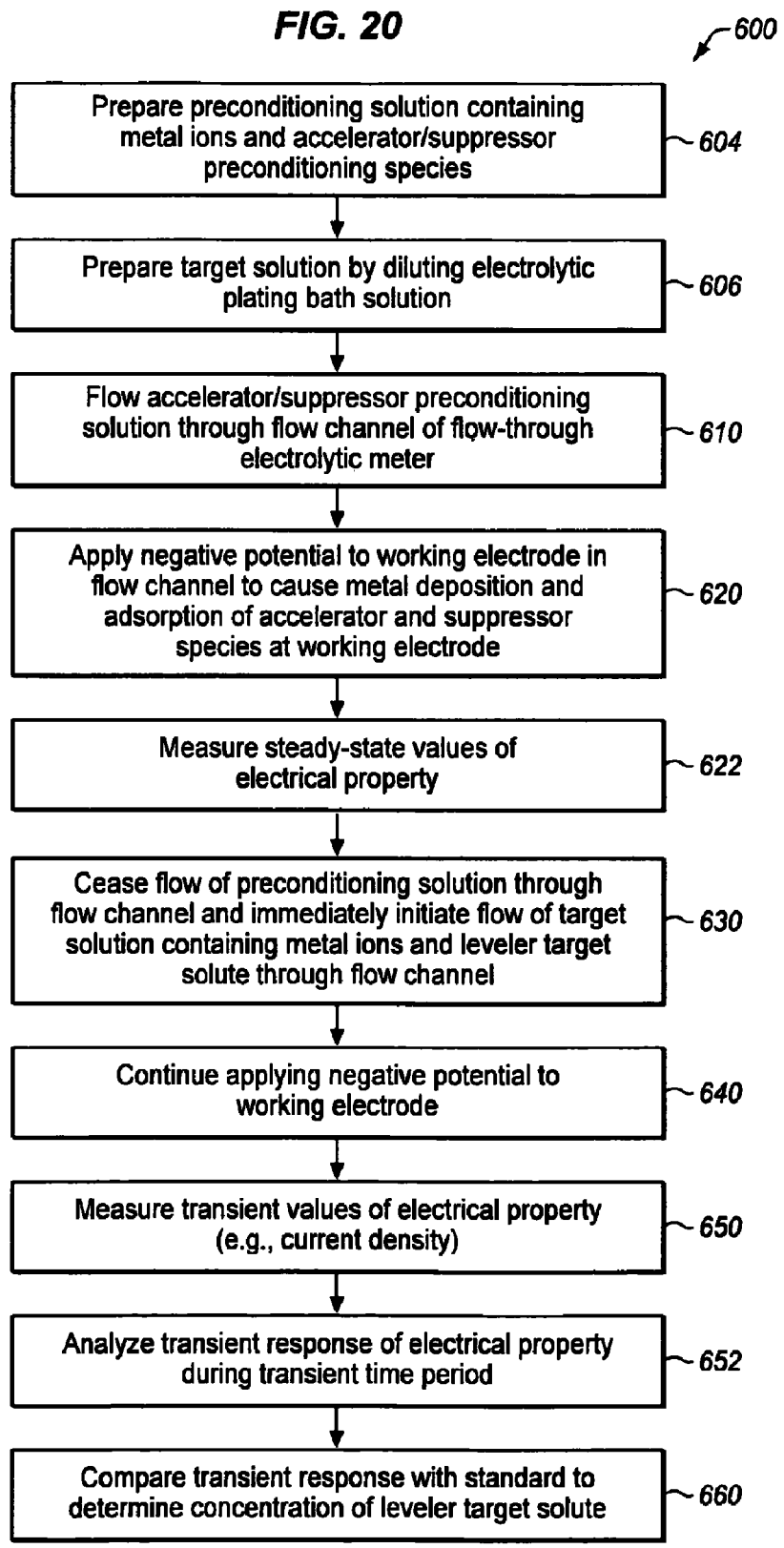
FIG. 20 contains a process flow sheet of a generalized method in accordance with the invention for measuring the concentration of leveler additive in an electrolytic copper plating solution.

FIG. 20 contains a process flow sheet 600 of a generalized method in accordance with the invention for measuring the concentration of leveler additive in an electrolytic copper plating solution. It is understood that some embodiments do not include all of the process steps of process flow sheet 600. For example, in some embodiments, it is not necessary to dilute the electroplating bath to make a target solution. Specific operating parameters, such as applied negative potential, compositions and concentrations of preconditioning and target solutions, and flow rates, included in the following description of process flow sheet 600 are applicable for target solute measurements comparable to those in Example 9. One of ordinary skill in the art will understand that measurements in accordance with the invention involving different conditions, such as different measuring equipment and different compositions and concentrations of electroplating bath solutions, will involve different operating parameters.

Process step 604 includes preparing a preconditioning solution containing metal ions and preconditioning accelerator species. In preferred embodiments, the preconditioning solution also includes suppressor species. A preconditioning solution preferably has sufficiently high concentration of accelerator species so that the working electrode of the flow-through electrolytic cell becomes saturated with accelerator species during the preconditioning phase. In some embodiments, an accelerator/suppressor preconditioning solution is prepared by adding a plating accelerator (e.g., a commercially available plating accelerator such as Enthone VIAFORM® EXTREME™ accelerator) and the plating suppressor (e.g., a commercially available plating suppressor such as Enthone VIAFORM® EXTREME™ suppressor) to a virgin electroplating solution, that is, to an electroplating solution (e.g., VMS, described above) that does not include any other organic plating attitudes. The concentration of accelerator additive in a preconditioning solution is typically (though not necessarily) greater than the concentration of accelerator in electroplating solutions actually used for bottom-filling. For example, the concentration of Enthone VIAFORM® EXTREME™ accelerator in electroplating bath used for bottom-filling is typically in the range of about from 5 mL/L to 15 mL/L. In contrast, in some embodiments, the concentration of Enthone VIAFORM® EXTREME™ accelerator in an accelerator/suppressor preconditioning solution is in a range of about from 15 mL/L to 40 mL/L.

A method for measuring leveler concentration typically (but not always) includes a process step 606, which comprises preparing a target solution by diluting an electrolytic plating bath solution with an appropriate base solution; for example, with an electrolytic solution containing no plating additives, such as VMS. The concentration of leveler in an electroplating solution commonly used for bottom-filling copper into features having high aspect ratios is sometimes higher than a preferred range of leveler concentrations in which the transient response (e.g., the change in current density over time) varies with concentration substantially independent of the concentration of other additives, such as accelerator and suppressor. For this reason, electroplating solution from an electroplating bath of an actual electroplating process may be diluted appropriately to lower leveler concentration to a desired transient-response measuring range. For example, when the electroplating bath solution has a suppressor concentration of about from 2.0 mL/L to 4 mL/L, it may be diluted with VMS by a factor of four to adjust the concentrations of suppressor, accelerator and leveler.

In some exemplary embodiments, the preconditioning solution comprises an organic plating accelerator comprising a functional species consisting essentially of bis-(3-sulfopropyl)-disulfide (SPS), and further comprises functional suppressor species consisting essentially of polyethylene glycol (PEG) polymers and polypropylene glycol (PPG) polymers (or block copolymers of the two) having an average molecular weight in a range of about from 1500 to 3500, at a molar ratio of PPG to PEG, PPG:PPE, in a range of about from 0.2 to 0.8. In some exemplary embodiments, the electrolytic preconditioning solution comprises plating accelerator comprising a functional species consisting essentially of bis-(3-sulfopropyl)-disulfide (SPS) at a concentration in a range of about from 30 ppm to 400 ppm, and further comprises a concentration of the functional suppressor species of PPG and PEG in a range of about from 25 ppm to 200 ppm.

Process step 610 includes flowing preconditioning solution containing accelerator (and preferably suppressor) through the flow channel of a flow-through electrolytic cell. In embodiments in which the flow-through electrolytic meter includes a flow-through electrolytic cell similar to electrolytic cell 100 described in Example 1, exemplary flow rates of preconditioning solution are in a range of about from 1 mL/min to 5 mL/min. Process step 620 includes applying negative potential to the working electrode in the flow channel to cause metal deposition and adsorption/activation of accelerator (and preferably suppressor) preconditioning species at the working electrode while preconditioning solution is flowing through the flow channel during the preconditioning phase. Representative durations of simultaneous process steps 610 and 620 during which negative potential is applied to the working electrode while preconditioning solution flows through the flow channel are 60 seconds to 150 seconds, although the exact duration time is usually not critical. Representative negative potential values at the working electrode are in a range of about from −0.1 to −0.5 V relative to the Ag/AgCl reference electrode. In preferred embodiments, process 600 includes process step 622 in which one or more substantially steady-state values of the electrical property (e.g., current density) are measured using the flow-through electrolytic meter before switching flow, although this steady-state measurement is not absolutely necessary.

Process step 630 includes switching the flow of liquid through the flow channel from accelerator-containing preconditioning liquid to the target solution that contains the leveler species. Process step 630, therefore, includes ceasing the flow of preconditioning solution through the flow channel and immediately initiating flow of target solution from the flow channel. Preferably, although not necessarily, switching the flow of liquid from the preconditioning solution to the target solution is effected in a switching time not exceeding one second, more preferably not exceeding 500 ms. Representative flow rates of target solution for the flow channel of an electrolytic cell similar to electrolytic cell 100 are in a range of about from 1 mL/min to 5 mL/min. Process step 640 includes applying negative potential during the target measuring phase, which begins when target solution begins flowing across the working electrode and continues. Representative negative potential values applied at the working electrode are in a range of about from −0.1 to −0.5 V relative to the reference electrode. Preferably, although not necessarily, the negative potential applied at the working electrode is the same during process step 620 (preconditioning phase) and process step 640 (target measuring phase). Preferably, although not necessarily, the negative potential applied to the working electrode is not interrupted during or between process steps 620 and 640.

Process step 650 includes measuring transient values of an electrical property, typically current density, during an initial transient time immediately after switching liquid flow in process step 630. In process 600, current density is measured at least a plurality of times, and preferably substantially continuously, during the transient time. Measurements of transient values of the current density by the flow-through electrolytic cell are performed generally at least for an initial transient time period during which the rate of change of transient values over time is substantial. A representative range of an initial transient time period is about five to 20 seconds, commencing immediately upon switching liquid flow in process step 630.

Process step 652 includes characterizing the transient response of the electrolytic measuring system by analyzing the plurality of transient values measured using the electrolytic cell. A representative calculation comprises calculating the rate of change of current density over time. For example, in the graph of FIG. 18, normalized values of current density were plotted as a function of time to determine a substantially linear rate of change (linear slope) for each of a plurality of leveler concentrations. Of course, as one of ordinary skill in the art will understand, the transient response used to characterize and measure accelerator concentration need not necessarily be a linear rate of change of an electrical property. For example, especially using computers, a characteristic transient response may be a characteristic nonlinear rate of change for a given concentration of accelerator. Additionally or alternatively in some embodiments, transient values of current density or other electrical property measured at given times during the target measuring phase are used to measure concentration.

Process step 660 comprises comparing the transient response calculated in process step 652 with one or more standard responses generated using known concentrations of target solute to determine the concentration of target solute. One of ordinary skill in the art will understand that standard responses for comparison in process step 660 are also generated using the process steps of process flow sheet 600. For example, response curves similar to those in FIG. 18 are useful as standards in process step 660 to compare with the transient response of an unknown target concentration of leveler in a target solution.

Figure 21:
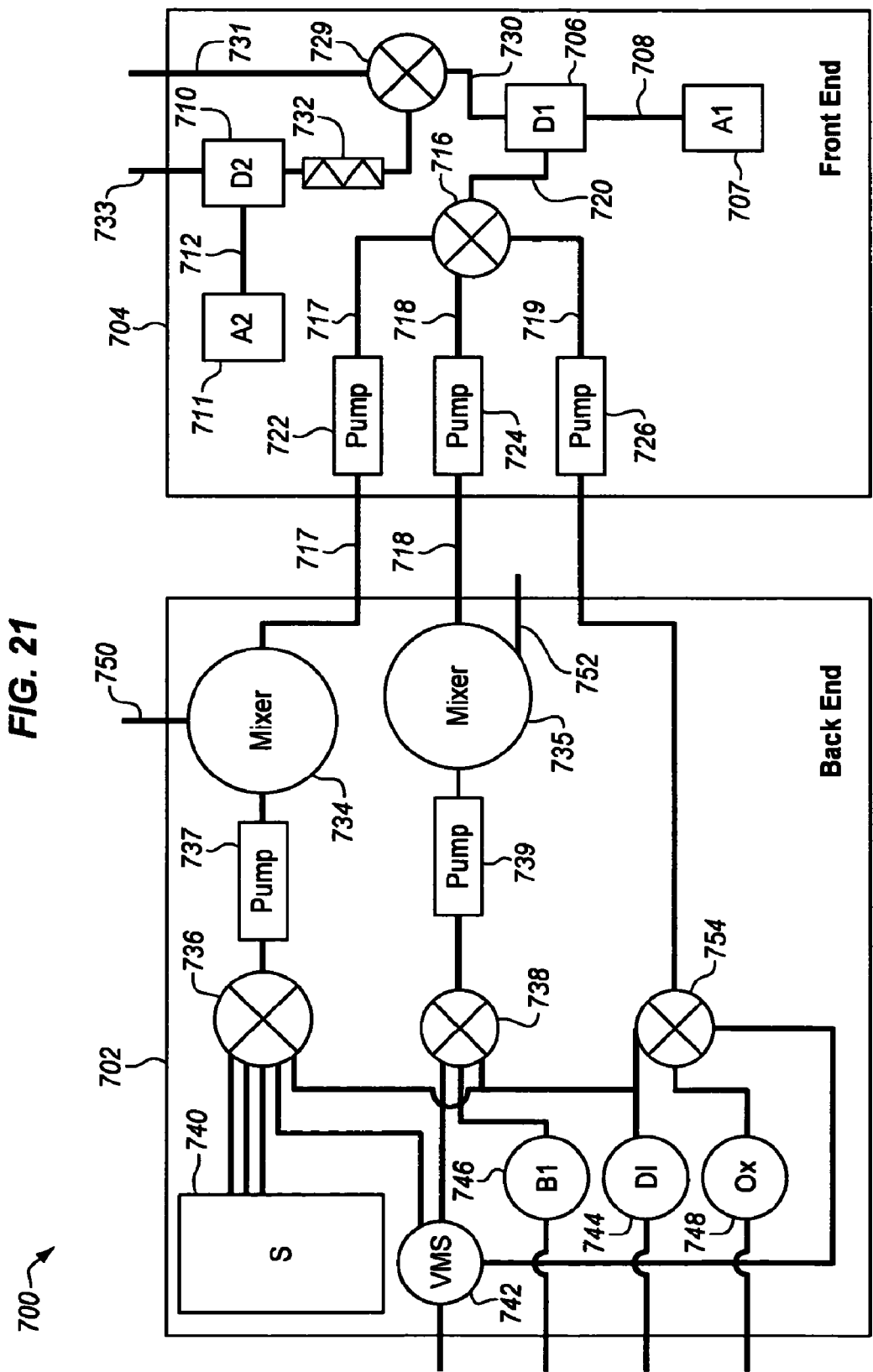
FIG. 21 contains a simplified diagram of an exemplary liquid delivery and detection system in accordance with the invention.
Figure 22:
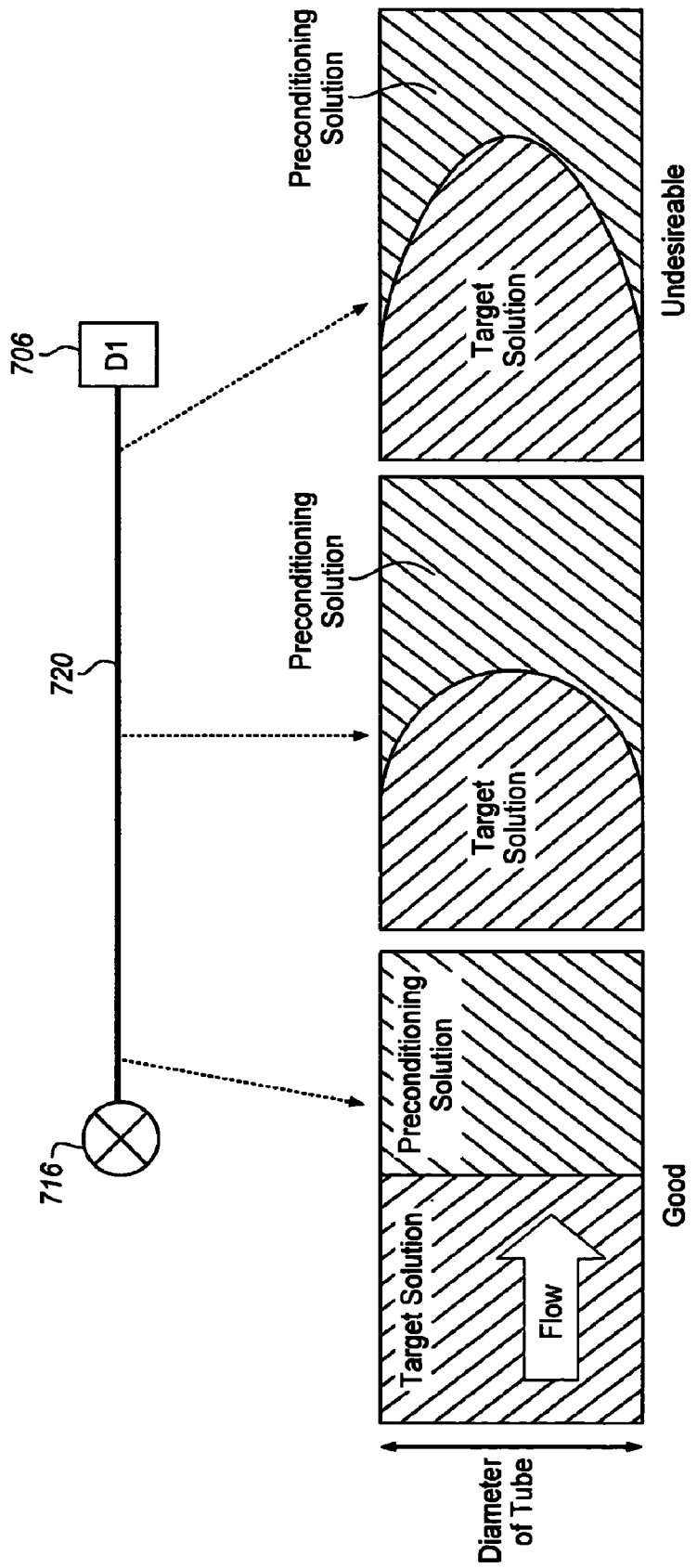
FIG. 22 depicts schematically the flow behavior of a preconditioning solution and a target solution through the channel inlet line leading to a flow-through electrolytic cell.

FIG. 21 contains a simplified diagram of an exemplary liquid delivery and detection system 700 in accordance with the invention. For purposes of description and explanation, system 700 is depicted in FIG. 21 as being divided into two sections, a mixing section 702 and a monitoring section 704, although actual systems in accordance with the invention may be organized and arranged differently. The diagram of FIG. 21 is meant to be a general description and does not represent actual representative sizes of various components included in the figure. Also, one of ordinary skill in the art will recognize that a system 700 in accordance with the invention includes a variety of ordinary and commonly used elements not depicted in the figure. Minimization of the total volume of a system 700 is important in some embodiments in which the system is mounted in a system module (not shown) on or proximate to a commercial electroplating tool. In preferred embodiments, a system module containing system 700 has a volume not exceeding about 1 cubic foot (ft) and all of the components are readily accessible for service.

As depicted in the FIG. 21, in monitoring section 704, system 700 includes a flow-through electrolytic detector cell 706 in accordance with the invention. An exemplary electrolytic detector cell 706 includes a flow-through electrolytic cell 100, described above with reference to FIGS. 2A and 2B. Electrolytic detector 706 is electrically connected to potentiostat 707 for measuring current and/or voltage. Wiring 708 between detector cell 706 and potentiostat 707 typically comprises a plurality of electrical wires for connecting a working electrode, a counter electrode and the reference electrode to the potentiostat. System 700 also is connected to peripheral equipment, such as a computer, for analyzing data collected using flow-through electrolytic cell 706. One of ordinary skill in the art will understand that in some embodiments, the potentiostat and other peripheral equipment used in the detection and analysis of data in accordance with the invention are located remotely from a system module and an electroplating tool.

System 700 depicted in FIG. 21 also includes inorganic detector 710 that is used for monitoring inorganic components of an electroplating solution, a density and/or conductivity meter 711 and electrical connection wires 712. Methods and systems for analysis of inorganic components of plating solutions are described in U.S. Pat. No. 6,458,262, issued to Reid et al. One of ordinary skill in the art will understand that inorganic detector 710 is not required in a system in accordance with the invention for monitoring organic additives.

System 700 comprises a switching valve 716. First inlet conduit 717 is connected to a first valve inlet, second inlet conduit 718 is connected to a second valve inlet, and third inlet conduit 719 is connected to a third valve inlet. A valve outlet of valve 716 is connected through channel inlet line 720 to the channel inlet port of detector cell 706. Switching valve 716 is operable to switch liquid flowing through channel inlet line 720 into flow-through detector 706 from liquid flowing in first inlet conduit 717 to liquid flowing in second inlet conduit 718. A pump 722 located inline with first inlet conduit 717 serves to pump electrolytic preconditioning solution from mixing section 702 to the first inlet of switching valve 716. A pump 724 located inline with second inlet conduit 718 serves to pump electrolytic target solution from mixing section 702 to the second valve inlet of switching valve 716. In preferred embodiments, switching valve 716 is operable to switch liquid flow through channel inlet line 720 into the flow channel of flow-through detector cell 706 from liquid flowing in first inlet conduit 717 to liquid flowing in second inlet conduit 718 within a switching time not exceeding one second. Preferably, the switching time does not exceed 500 ms. In more preferred embodiments, the switching time does not exceed 200 ms, and in even more preferred embodiments, the switching time does not exceed 100 ms. It is important that channel inlet line 720 have a short length. Good measurements in accordance with the invention rely on a fast and efficient transition of flow over the working electrode of the solutions coming through inlet conduits 717, 718. FIG. 1 depicts an ideal transition of liquid flow having a clearly defined vertical interface between preconditioning solution 1 and target solution 2. In reality, as a result of fluid dynamics and mass transfer, the flow of target solution 2 through channel inlet line 720 disperses axially down the tube as it travels. This flow behavior is depicted schematically in FIG. 22. The effect becomes more prominent as tube length increases. Minimizing the tube length of channel inlet line 720 minimizes the type of dispersion depicted in FIG. 22. In some embodiments, channel inlet line 720 consists of tubing having an inside diameter of 1/16-inch and a length of about 3 inches. Preferably, the length of channel inlet line 720 is less than 3 inches. More preferably, the channel inlet port of electrolytic detector cell 706 connects directly to the outlet of valve 716. Since pumps 722, 724 are used to pump the preconditioning solution and the target solution, they preferably possess several characteristics. Wetted parts of pumps 722, 724 preferably are electrically isolated from the pump motor and are able to withstand corrosive environments, such as VMS and plating solutions containing organic additives. Preferably, pumps 722, 724 provide a steady flow rate in a range of about from 0.1 mL/min to 10 mL/min and possess a quick start/stop response time (100 milliseconds or less), comparable to the properties of the model mzr-2942 gear pumps, discussed above with reference to pumps 220, 222 in system 200 in FIG. 3. In contrast, commercially available syringe pumps often are not able to provide sufficiently steady flow rate and are more prone to failure. Pump 726 serves to pump cleaning and rinsing liquids through various portions of detection section 704, particularly through electrolytic detection cell 706. During cleaning and rinsing, pump 726 pumps cleaning and rinsing liquids through inlet conduit 719 and valve 716 to detector 706. An exemplary cleaning liquid is the oxidizing cleaning solution described above, which contains sulfuric acid, hydrogen peroxide and deionized water. Accordingly, the wetted parts of pumps 726 should be made from non-corrosive material. Since pump 726 is used simply to flow cleaning and rinsing solutions, the requirements for steady flow rate and response time are not as important as with pumps 722, 724.

System 700 also includes a valve 729 that receives target solution from the channel outlet of detector cell 706 through channel outlet line 730. Valve 729 serves to direct target solution either to a disposal system through exit line 731 or to inorganic detector 710, preferably through filter 732. The output of inorganic detector 710 typically flows to a disposal system through an exit line 733.

System 700 comprises preconditioner mixer 734 and target mixer 735 in mixing section 702. A preconditioner valve 736 serves to control the flow of liquids to preconditioner mixer 734. Pump 737 serves to pump liquids from various liquid sources to preconditioner mixer 734. A target liquid valve 738 serves to control the flow of liquids to target mixer 735. Pump 739 serves to pump liquids from various liquid sources to target mixer 735.

An organic source subsection 740 includes a plurality of sources of organic plating additives. Preferably, organic source subsection 740 is implemented as a module suitable for "plug-and-play" (such as with a color printer cartridge). During operation in accordance with the invention to measure an unknown target concentration, one or more organic plating additives are mixed with VMS from VMS source 742 to make preconditioning solutions having known amounts of non-target additives. During operation in accordance with the invention, a target solution is prepared in target mixer 732 by pumping VMS from VMS source 742 and electroplating bath solution from electroplating bath source 746. Similarly, organic plating additives are mixed with VMS from VMS source 742 to make preconditioning solutions and target solutions having known amounts of additives for the purpose of measuring standard responses to known concentrations of organic target solute. During some cleaning and rinsing operations, oxidizing cleaning solution and/or deionized water is pumped from DI source 744 and cleaning solution source 748 through electrolytic detector cell 706 and through other portions of system 700. Exit line 750 leads from mixer 734 to a disposal system. Similarly, exit 752 leads from mixer 735 to a disposal system. A cleaner valve 754 serves to control the flow of cleaning and rinsing liquids to pump 726. One of ordinary skill in the art will understand that selective use of the valves and pumps in system 700 allows rinsing and cleaning of substantially all portions of system 700.

The main function of pumps 737, 739 is to pump specified amounts of liquids from their respective sources into mixers 734, 735, respectively. Similar to pumps 722, 724, pumps 737, 739 must be operable to provide precisely controlled amounts of small volumes of fluids used in electrolytic detector cell 706. Representative volumes of liquids pumped into mixers 734 and 735 are in a range of about from 100 microliters (µL) to 100 mL. Representative examples of pumps 737, 739 are the model mzr-2942 gear pumps commercially available from HNP Mikrosysteme GmbH. A mzr-2942 gear pump is operable to deliver reliably and precisely a dose volume down to 0.5 µL and up to 100 mL.

In some embodiments, pumps 737, 739 are operable to draw liquids from their sources through valves 736, 738, respectively. Some embodiments, however, include additional pumps not shown upstream from mixers 734, 735 that function to pump liquids from the various liquid sources.

Valve 736 is a six-port valve having five input ports and one output port. Due to the sensitivity of the measurements conducted in electrolytic detector cell 706, contact with each other of the liquids in the input lines leading into valve 736 must be minimized. A suitable valve 736 is a model RHEODYNE® TITAN®EX MLP777-605 valve commercially available from IDEX® Corporation, with a six-position, seven-port selector. A similar valve is suitable for use as valve 738. The speed of valves 736, 738 is not as important as the speed of valve 716 because these valves will not be used for analytical measurement, but simply for switching between incoming liquids to the mixers.

Figure 23:
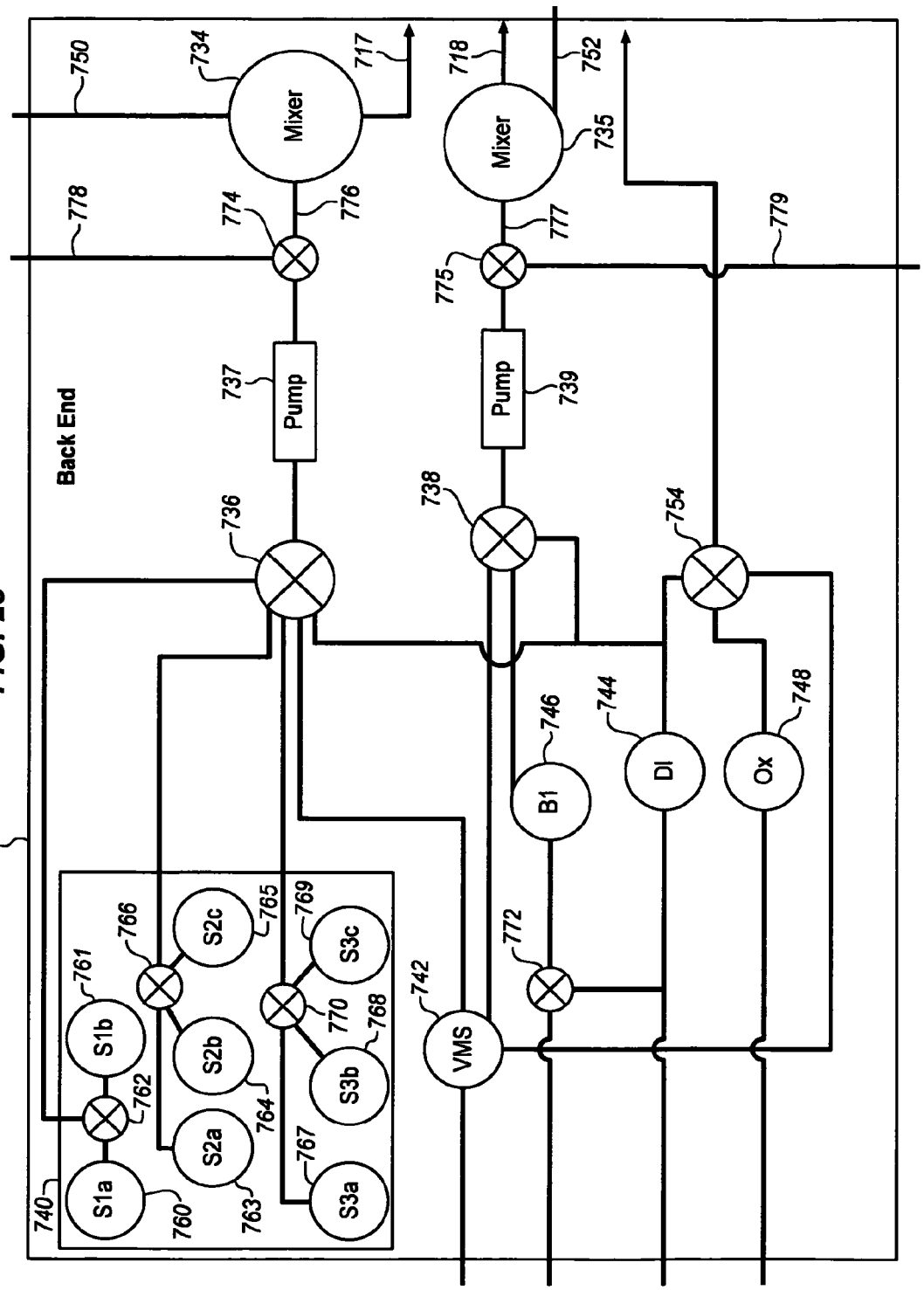
FIG. 23 depicts schematically a detailed representation of the mixer section in the system of FIG. 21.

FIG. 23 depicts schematically a more detailed representation of mixer section 702. In some preferred embodiments, a system 700 includes a plurality of small tanks located in organic source module 740 that serve as sources of organic additive of varying concentrations. As depicted in FIG. 23, organic source module 740 contains accelerator sources 760 and 761. In some embodiments, accelerator source 760 contains organic plating accelerator at a standard concentration delivered by a chemical vendor, and accelerator source 761 contains accelerator solution that has been diluted by a factor of 10. Accelerator source valve 762 controls liquid flow between sources 760, 761 and valve 736. Suppressor additive sources 763, 764 and 765 connected to suppressor source valve 766 contain suppressor solution at standard vendor concentration, at 10 times dilution, and at 100 times dilution, respectively. Similarly, leveler additive sources 767, 768 and 769 connected to leveler source valve 770 contain leveler solution at standard vendor concentration, at 10 times dilution, and at 100 times dilution, respectively. The availability of several different concentrations allows more accurate dosing of the additives during measurement operations in consideration of small defined operating ranges of the pumps, such as pumps 737, 739. Preferably, standard solutions are replaced on a periodic basis; for example, once every one or two months. In preferred embodiments, the volume of each additive source in module 740 is about 25 mL. In a representative embodiment: oxidizing source 748 is a holding tank having a volume of about 100 mL and is corrosion resistant; VMS source 742 is resistant to VMS and has a tank volume of about 200 mL; the volume of electroplating bath source 746 is about 10 mL; and the volume of Dl water source 744 is about 200 mL. Source tanks 742, 744, 746 and 748 are essentially holding tanks that are supplied and replenished by connections to corresponding liquid supplies exterior to mixer section 702.

Each set of measurements of organic additives requires a new bath sample to be drawn into bath source 746 from the electroplating tool. Bath source 746 is thoroughly washed with Dl water every time prior to pulling a bath sample. Valve 772 is used to allow Dl water to run into bath source 746 for rinsing. Valves 774, 775 are used to purge the tubing leading up to mixers 734, 735, respectively, and to distribute fluid from pumps 737, 739 to the mixers. The distance of these valves to the respective entrance of mixers 734, 735 is important because this distance defines how much "leftover" liquid gets dumped into a mixer when fluids are purged and changed. In a representative embodiment, each of mixers 734, 735 is operable to accept liquid volumes in a range of about from 5 mL to 150 mL.

Organic additives are surfactants and often adsorb strongly to metal surfaces. These additives include disulfides and polyethers. Accordingly, the inside surfaces of tanks, tubing, pumps and valves coming in contact with additives preferably are polymer materials that are not susceptible to absorption by these types of materials.

Mixing section 702 contains a large amount of tubing to allow for proper routing of the various liquids. The lengths of the various sections of tubing are minimized to minimize the pressure requirements of the pumps. Additionally, tubing length is minimized to reduce the amount of liquid and the time required to purge and rinse the various sections of tubing.

Liquid in the tubing between valves 736 and mixer 734, as well as between valve 738 and mixer 735, must be flushed to remove liquid from a previous measurement before new solutions are added to the mixers. This is done by closing the valve connection of valve 774 to mixer 734 and flowing Dl water or other flushing liquid through valve 774 and exit line 778, and similarly by closing the valve connection of valve 775 to mixer 735 and flowing Dl water or other flushing liquid through valve 775 and exit line 779. When these flushing operations are performed, a certain amount of liquid remains in the tubing of lines 776 and 777. Accordingly, the volumes of the liquid tubing in line 776, 777 between valves 774, 775 and mixers 734, 735, respectively, are minimized (and ideally are zero). Since the smallest representative doses of pumps 737, 739 are about 100 μL, the volume of tubing of each of lines 776, 777 preferably does not exceed the smallest expected dosing volume of about 100 μL. Therefore, with tubing having 1/16-inch inside diameter, the length of lines 776, 777 does not exceed about 5 cm. To reduce the amount of flushing liquid used between measurements with different solutions, the lengths of tubing between valve 736 and mixer 734, as well as between valves 738 and mixers 735, are minimized.

Methods and systems in accordance with the invention are useful in a wide variety of circumstances and applications. It is evident that those skilled in the art may now make numerous uses and modifications of the specific embodiments described, without departing from the inventive concepts. It is also evident that the steps recited may, in some instances, be performed in a different order; or equivalent structures and processes may be substituted for the structures and processes described. For example, as mentioned above, in some embodiments, concentration measurements in accordance with the invention may be conducted by measuring transient values of voltage change when constant current is applied in an electrolytic cell. Since certain changes may be made in the above systems and methods without departing from the scope of the invention, it is intended that all subject matter contained in the above description or shown in the accompanying drawings be interpreted as illustrative and not in a limiting sense. Consequently, the invention is to be construed as embracing each and every novel feature and novel combination of features present in or inherently possessed by the methods and structures described in the claims below and by their equivalents.

The invention claimed is:

1. A method of ascertaining the concentration of a target solute in an electrolytic solution, comprising steps of:
    (a) flowing an electrolytic preconditioning solution containing metal ions and a preconditioning species through a flow channel of a flow-through electrolytic meter;
    (b) causing deposited metal and adsorbed preconditioning species to form on a working electrode located in said flow channel by applying a potential to said working electrode;
    (c) then ceasing flow of said preconditioning solution through said flow channel;
    (d) immediately after said ceasing flow of preconditioning solution, initiating flow of an electrolytic target solution through said flow channel, said electrolytic target solution including metal ions and a target concentration of said target solute;
    (e) during a transient time period immediately after said initiating flow, applying a constant potential to said working electrode and measuring current density; and
    (f) determining a slope of current density from a linear portion of a current density-time dependence measured during said transient time period and determining said target concentration from said slope of current density.

2. The method of claim 1 wherein said method does not comprise stripping said deposited metal and said adsorbed preconditioning species prior to said initiating flow of an electrolytic target solution and prior to said transient time period.

3. A method of claim 1, wherein said determining said target concentration from said slope of current density further comprises:
    ascertaining said target concentration of said target solute in said target solution by comparing said target slope of current density with one or more standard slopes of current density corresponding to known concentrations of said target solute.

4. The method of claim 1 wherein:
    an interaction of said target solute with said preconditioning species during said transient time period affects said slope of current density.

5. The method of claim 1, further comprising:
    before said step (d), mixing a bath solution containing said target solute with a base liquid to form said electrolytic target solution.

6. The method of claim 5 wherein said mixing dilutes a concentration of said preconditioning species in said bath solution.

7. The method of claim 1, further comprising:
before said step (d), adding an activator species to a bath solution containing a target solute precursor to form said target solute.

8. The method of claim 1 wherein said ceasing flow of preconditioning solution in step (c) and said initiating flow of electrolytic target solution in step (d) comprise:
switching liquid flow to said working electrode in said flow channel from said preconditioning liquid to said electrolytic target solution within a switching time not exceeding 500 milliseconds.

9. The method of claim 1 wherein said ceasing flow of preconditioning solution in step (c) and said initiating flow of electrolytic target solution in step (d) comprise:
switching liquid flow through a flow valve from a preconditioning liquid to an electrolytic test solution, wherein said flow valve comprises a first inlet port, a second inlet port and an outlet port, and said outlet port is fluidically connected to said flow channel of said flow-through electrolytic meter.

10. The method of claim 1 wherein:
said preconditioning species comprises an organic plating suppressor; and
said target solute comprises an organic plating accelerator.

11. The method of claim 10 wherein:
said electrolytic preconditioning solution comprises functional suppressor species consisting essentially of polyethylene glycol (PEG) polymers and polypropylene glycol (PPG) polymers having an average molecular weight in a range of about from 1500 to 3500, at a molar ratio of PPG to PEG, PPG:PPE, in a range of about from 0.2 to 0.8;
said organic plating accelerator comprises a functional species consisting essentially of bis-(3-sulfopropyl)-disulfide (SPS).

12. The method of claim 10 wherein:
said electrolytic preconditioning solution has a concentration of said functional suppressor species of PPG and PEG in a range of about from 50 ppm to 1500 ppm; and
said initiating flow of electrolytic target solution in step (d) comprises flowing a target solution comprising bis-(3-sulfopropyl)-disulfide (SPS) at a concentration in a range of about from (10 ppm to 100 ppm)/2.

13. The method of claim 12, further comprising:
before said step (d), mixing an electrolytic plating bath solution from an electrolytic plating bath with a base liquid to form said electrolytic target solution;
wherein said base liquid consists essentially of virgin electrolytic plating solution having substantially no organic plating additives; and
wherein said mixing dilutes concentrations of solutes of said electrolytic plating bath solution by a factor of about two.

14. The method of claim 1 wherein:
said preconditioning species comprises a chloride ion;
said electrolytic preconditioning solution is substantially free of organic plating additives; and
said target solute consists essentially of an organic plating suppressor.

15. The method of claim 14 wherein:
said preconditioning species comprises chloride ion (Cl$^-$); and
said target solute comprises functional suppressor species consisting essentially of polyethylene glycol (PEG) polymers and polypropylene glycol (PPG) polymers having an average molecular weight in a range of about from 1500 to 3500, at a molar ratio of PPG to PEG, PPG:PPE, in a range of about from 0.2 to 0.8.

16. The method of claim 15 wherein:
said electrolytic preconditioning solution has a chloride ion concentration in a range of about from (10 ppm to 500 ppm); and
said initiating flow of electrolytic target solution in step (d) comprises flowing a target solution comprising a concentration of said functional suppressor species of PPG and PEG at a concentration in a range of about from (50 ppm to 600 ppm)/32.

17. The method of claim 16, further comprising:
before said step (d), mixing an electrolytic plating bath solution from an electrolytic plating bath with a base liquid to form said electrolytic target solution;
wherein said base liquid consists essentially of virgin electrolytic plating solution having substantially no organic plating additives; and
wherein said mixing dilutes concentrations of solutes of said electrolytic plating bath solution by a factor of about thirty-two.

18. The method of claim 1 wherein:
said preconditioning species comprises an organic plating accelerator; and
said target solute consists essentially of an organic plating leveler.

19. The method of claim 18 wherein:
said preconditioning species further comprises an organic plating suppressor.

20. The method of claim 19 wherein:
said preconditioning species comprises an organic plating accelerator comprising a functional species consisting essentially of bis-(3-sulfopropyl)-disulfide (SPS), and further comprises functional suppressor species consisting essentially of polyethylene glycol (PEG) polymers and polypropylene glycol (PPG) polymers having an average molecular weight in a range of about from 1500 to 3500, at a molar ratio of PPG to PEG, PPG:PPE, in a range of about from 0.2 to 0.8; and
said target solute comprises an organic leveler comprising functional species poly(vinyl pyrrolidone (PVP) having an average molecular weight in a range of about from 3,000/4 to 5,000/4.

21. The method of claim 20 wherein:
said electrolytic preconditioning solution comprises plating accelerator comprising a functional species consisting essentially of bis-(3-sulfopropyl)-disulfide (SPS) at a concentration in a range of about from 30 ppm to 400 ppm, and further comprises a concentration of said functional suppressor species of PPG and PEG in a range of about from 25 ppm to 200 ppm.

22. The method of claim 21, further comprising:
before said step (d), mixing an electrolytic plating bath solution from an electrolytic plating bath with a base liquid to form said electrolytic target solution;
wherein said base liquid consists essentially of virgin electrolytic plating solution having substantially no organic plating additives; and
wherein said mixing dilutes concentrations of solutes of said electrolytic plating bath solution by a factor of about four.

23. The method of claim 1, wherein one constant potential is applied to the working electrode continuously during steps (b)-(e).

* * * * *